United States Patent [19]

Baba et al.

[11] Patent Number: 5,878,108
[45] Date of Patent: Mar. 2, 1999

[54] METHOD FOR GENERATING X-RAY IMAGE AND APPARATUS THEREFOR

[75] Inventors: Rika Baba, Kokubunji; Ken Ueda, Kashiwa; Ken Ishikawa, Matsudo; Hironori Ueki, Kokubunji; Keiji Umetake, Inagi, all of Japan

[73] Assignee: Hitachi Medical Corporation, Tokyo, Japan

[21] Appl. No.: 80,223

[22] Filed: May 18, 1998

Related U.S. Application Data

[63] Continuation-in-part of Ser. No. 759,088, Nov. 29, 1996.

[30] Foreign Application Priority Data

Nov. 30, 1995 [JP] Japan ................................ 7-31184
May 19, 1997 [JP] Japan ................................ 9-128404

[51] Int. Cl.$^6$ ........................ H05G 1/64; A61B 6/03
[52] U.S. Cl. ........................ 378/98.4; 378/7; 378/901
[58] Field of Search .................. 378/7, 98.4, 901, 378/62

[56] References Cited

U.S. PATENT DOCUMENTS

| | | | |
|---|---|---|---|
| 4,718,076 | 1/1988 | Doi et al. | 378/146 |
| 4,841,555 | 6/1989 | Doi et al. | 378/98.4 |
| 4,918,713 | 4/1990 | Honda | 378/98.4 |
| 5,327,476 | 7/1994 | Kemner | 378/98.4 |
| 5,774,521 | 6/1998 | Close et al. | 378/98.4 |

OTHER PUBLICATIONS

Medical Physics, vol. 12, No. 3, May/Jun. 1985, "Removal of Image Intensifier Veiling Glare by Mathematical Deconvolution Techniques", J. Seibert et al, pp. 281–288.
Medical Physics, vol. 15, No. 4, Jul./Aug. 1988, "X–ray Scatter Removal by Deconvolution", J. Seibert et al, pp. 567–575.
Medical Physics, vol. 15, No. 3, May/Jun. 1988, "Scatter–glare Corrections in Quantitative Dual–Energy Fluoroscopy", Molloi et al, pp. 289–297.
Medical Physics, vol. 20, No. 1, Jan./Feb. 1993, "A Technique of Scatter–Glare Correction Using a Digital Filtration", M. Honda et al, pp. 59–69.
Medical Physics, vol. 18, No. 2, Mar. Apr. 1991, "Method for Estimating the Intensity of Scattered Radiation Using a Scatter Generation Model", M. Honda et al, pp. 219–226.
K. Sekihara et al, "Cone–Beam CT Angiography", JAMIT Frontier 95. (1995), pp. 23–28. No month.

(List continued on next page.)

*Primary Examiner*—Don Wong
*Assistant Examiner*—David Vernon Bruce
*Attorney, Agent, or Firm*—Fay, Sharpe, Beall, Fagan, Minnich & McKee

[57] ABSTRACT

A radiographic apparatus which can improve at high speed the picture quality of an X-ray fluoroscopic image or an X-ray radiographic image is disclosed. In a radiographic apparatus acquiring an X-ray fluoroscopic image or an X-ray radiographic image and having a scattered X-ray corrector for eliminating a scattered X-ray component from the acquired X-ray fluoroscopic image or X-ray radiographic image, the scattered X-ray corrector comprises: scattered X-ray intensity distribution function generator for generating a scattered X-ray intensity distribution function on the basis of the acquired X-ray fluoroscopic image or X-ray radiographic image; a moving average calculator for executing moving average calculation a plurality of times in each of the vertical and lateral directions of the acquired X-ray fluoroscopic image or X-ray radiographic image; a window width calculator for calculating a window width of the moving average calculation on the basis of the scattered X-ray intensity distribution function; and a difference calculator means for calculating the difference between the acquired X-ray fluoroscopic image or X-ray radiographic image and an image to which the moving average calculation is performed.

11 Claims, 23 Drawing Sheets

OTHER PUBLICATIONS

M. Honda, "A Technique of Scatter–glare Correction Using a Digital Filtration", Medical Physics. vol. 20(1), (Jan./Feb. 1993) pp. 59–69.

R. Baba et al, "Analysis and Correction of Veiling Glare and Scattered Radiation on X–ray 11 TV–Camera System", Medical Imaging Technology. vol. 14, No. 4 (Jul. 1996) pp. 383–384.

| FLUOROGRAPHIC IMAGE | 1 | 2 | 3 | 4 | 5 | 6 | 7 | 8 | 9 | 10 | 11 | 12 |
|---|---|---|---|---|---|---|---|---|---|---|---|---|
| DISPLAYED IMAGE | 1 | 2 | 3 | 4 | 5 | 6 | 7 | 8 | 9 | 10 | 11 | 12 |
| VEILING-GLARE AND SCATTERED X-RAY COMPONENT IMAGE FOR DIFFERENCE | — | — | — | — | 1 | 1 | 1 | 1 | 5 | 5 | 5 | 5 |
| IMAGE DURING CALCULATION PROCESS TO OBTAIN VEILING-GLARE AND SCATTERED X-RAY COMPONENT IMAGE | 1 | 1 | 1 | 1 | 5 | 5 | 5 | 5 | 9 | 9 | 9 | 9 |

METHOD FOR GENERATING X-RAY IMAGE AND APPARATUS THEREFOR

CROSS-REFERENCE TO RELATED APPLICATION

This application is a continuation-in-part of prior application 08/759,088, filed Nov. 29, 1996 and now pending.

BACKGROUND OF THE INVENTION

The present invention relates to a method for generating an X-ray image and an apparatus thereof for correcting a blur of a fluorographic image or radiographic image.

A fluorographic image or radiographic image obtained by an ordinary fluorographic device includes a blur generally and to obtain a more desirable fluorographic image or radiographic image, a correction process of removing this blur is necessary. Firstly, the cause of blur occurrence will be explained.

In radiography or fluorography, the intensity distribution of X-ray passing through a subject to be inspected is converted to an optical image by an X-ray image sensor and the optical image is recorded on a film or the optical image is electrically read by a TV camera and displayed and recorded digitally.

For example, in radiography, there are direct radiography using an X-ray intensifying screen and an X-ray film and indirect radiography using an optical system comprising an X-ray phosphor plate, lens, and mirror and a film. In real-time fluorography, there is a method for forming an optical image of the intensity distribution of X-ray converted by an X-ray phosphor plate and an X-ray image intensifier on the imaging surface of an imaging tube using an optical system such as a lens and electrically reading it.

FIG. 2 shows a typical X-ray detection system of the prior art using an X-ray image intensifier (hereinafter abbreviated to XII). Among X-rays irradiated from an X-ray tube 101, the intensity distribution of X-rays on the input surface of an XII 103 by direct X-ray 111 passing through a subject 110 and an anti-scatter grid 102 is converted to an optical image on an output phosphor screen 104 of the XII 103 by scanning of an electron beam 109 and this optical image is formed on an imaging device 106 using a lens and a mirror 105 and electrically read.

On the output phosphor screen 104, a diffusion light 108 which is called a veiling glare caused by a light diffusion phenomenon is generated in addition to a direct light 107 and an image by the original X-ray intensity distribution is blurred. Generally in a method that the X-ray intensity distribution (X-ray image) is converted to an optical image and then the optical image is optically measured, a phenomenon that in a phosphor medium generating an optical image, the original X-ray image is blurred by the light diffusion phenomenon cannot be avoided. The blur due to veiling glare affects strongly as the reduction rate of an X-ray image in a phosphor medium increases. The veiling glare 108 in the XII 103 causes a reduction of the image contrast.

Another cause of blur in addition to the veiling glare 108 is a scattered X-ray 112 by the subject 110. This scattered X-ray 112 travels in a direction different from that of an X-ray beam (hereinafter abbreviated to "direct X-ray") 111 emitted from the X-ray tube. Scattering of X-rays due to a subject is always generated, so that when a scattered X-ray is detected by an X-ray image sensor, the X-ray intensity distribution on the surface of the X-ray image sensor is blurred. Generally, the anti-scatter grid 102 is arranged on the front of an X-ray image detector so as to shield a scattered X-ray. However, all scattered X-rays entering the grid cannot be shielded and a measured image includes a blur due to the scattered X-ray. To the image on the surface of the X-ray image detector including the blur due to a scattered X-ray, a blur due to the veiling glare 108 in the aforementioned phosphor medium is added furthermore.

As explained above, in the method for converting an X-ray image to an optical image and measuring it optically, the blur on the surface of X-ray image sensor caused by a scattered X-ray by a subject and the blur due to the veiling glare in the phosphor medium reduce the image quality.

The related prior art for correcting a blur due to veiling glare and a blur due to scattered X-ray will be explained hereunder.

(1) An art for correcting a blur due to veiling glare in an XII by the direct deconvolution method is disclosed in the reference by Seibert and others (Medical Physics, Vol. 12, p. 281 to 288 (1985), Literature 1). An art for correcting a blur due to veiling glare and then correcting a blur due to scattered X-ray by the direct deconvolution method is disclosed in another reference by Seibert and others (Medical Physics, Vol. 15, p. 567 to 575 (1988), Literature 2). A degradation model and a correction process by the aforementioned correction methods of the prior arts are shown in FIGS. 3A and 3B. In the degradation model, the image blurring process due to scattered X-ray is expressed by a convolution 203 of a point spread function including scattered X-ray component 202 and an ideal image (virtual image excluding a blur due to scattered X-ray and a blur due to veiling glare) 201. Furthermore, the blurring process due to veiling glare is expressed by a convolution 206 of a point spread function (abbreviated to PSF (point spread function)) including veiling glare component 205 and a blurred image by scattered X-ray 204.

The outline of the correction process according to the degradation model is described below. By a deconvolution 209 which is introduced from an exponential function expressing the veiling glare component of the point spread function and uses a deconvolution filter for veiling glare 208, a veiling glare corrected image 210 correctted a blur due to veiling glare is generated. Furthermore, by a deconvolution 212 which is introduced from a normal distribution function expressing the scattered X-ray component of the point spread function and uses a deconvolution filter for scattered X-ray 211, a corrected image 213 corrected blurs due to veiling glare and scattered X-ray is generated. The deconvolution is processed by performing the two-dimensional inverse Fourier transformation for the multiplication result of the two-dimensional Fourier transformation result of an image to be processed and the deconvolution filter. The deconvolution filter for veiling glare 208 includes the intensity ratio of veiling glare to direct light hereinafter abbreviated to "veiling glare intensity ratio") as a parameter. The deconvolution filter for scattered X-ray 211 includes the intensity ratio of scattered X-ray to direct X-ray (hereinafter abbreviated to "scattered X-ray intensity ratio") as a parameter. The veiling glare intensity ratio of the XII is obtained beforehand. The scattered X-ray intensity ratio is estimated by searching a look-up table prepared for each measurement condition beforehand from the value of measured image. The look-up table is generated beforehand for each X-ray tube voltage, thickness of subject, anti-scatter grid, diameter of field of view, and geometry for measurement.

(2) A prior art for correcting by the blurred image formation method is disclosed in the reference by Molloi and others (Medical Physics, Vol. 15, p. 289 to 297 (1988), Literature 3) and in the reference by Honda and others (Medical Physics, Vol. 20, p.59 to 69(1993), Literature 4). A degradation model and a correction process by the correction method using the aforementioned image formation method of the prior art are shown in FIGS. 4A and 4B. In the degradation model, the blurring process due to scattered X-ray and the blurring process due to veiling glare are integrated.

A product (hereinafter abbreviated to "veiling glare and scattered X-ray intensity distribution function") 304 of a sum intensity ratio of veiling glare and scattered X-ray component to direct X-ray component (hereinafter abbreviated to "veiling glare and scatter sum ratio") 302 and a point spread function of sum of scattered X-ray and veiling glare (hereinafter abbreviated to "point spread function of scattered X-ray and veiling glare") 303 is generated, and a blurred image 306 comprising a component in which veiling glare and scattered X-ray are integrated(hereinafter abbreviated to "image of scattered X-ray and veiling glare component") is generated from a convolution 305 of the product 304 and an ideal image 301, and a measured image 308 is expressed by addition 307 of the image of scattered X-ray and veiling glare component 306 and the ideal image 301.

The outline of the correction process according to the degradation model is described below. An image of scattered X-ray and veiling glare component 310 is generated from a deconvolution 309 of the product 304 and the measured image 308. The corrected image 302 is generated by subtracting 311 the image of scattered X-ray veiling glare component 310 from the measured image 308. With respect to the deconvolution 309, the convolution method is disclosed in the reference by Molloi and others and the Fourier transformation method is disclosed in the reference by Honda and others. In the deconvolution 309 in the convolution method, a two-dimensional convolution of the veiling glare and scattered X-ray intensity distribution function 304 and the measured image 308 is performed The deconvolution 309 in the Fourier transformation method is performed as indicated below. As a function of the product of the two-dimensional Fourier transformation of each of the veiling glare and scatter sum ratio 302 and the point spread function thereof 303, a deconvolution filter in the spatial frequency space is obtained. The result of multiplication of the two-dimensional Fourier transformation of the measured image 308 by the deconvolution filter is subjected to the two-dimensional inverse Fourier transformation.

The veiling glare and scatter sum ratio is a function of the value of measured image, X-ray tube voltage for measurement, thickness of subject, anti-scatter grid, diameter of field of view, and distance between subject and grid (air gap and others).

As a veiling glare and scatter sum ratio decision method, a method for obtaining the ratio by searching a look-up table prepared for each measurement condition beforehand from the value of measured image is disclosed in the aforementioned reference by Molloi and others.

As another decision method, a method for calculating the ratio by searching the table and processing from the maximum value of measured image and the measurement condition is disclosed in the aforementioned reference by Honda and others and another reference by Honda and others (Medical Physics, Vol. 18, p. 219 to 226 (1991),Literature 5).

As explained above, the blur usually occurs in an X-ray fluoroscopic image and an X-ray radiographic image directly obtained by using a conventional radiographic apparatus. In order to obtain inherent X-ray fluoroscopic image and X-ray radiographic image, a correction process for eliminating the blur is necessary.

In a method of transforming an X-ray image to an optical image and measuring the optical image, the blur occurring on an X-ray image sensor face by a scattered X-ray inside the subject and a blur caused by a veiling glare in an optical image formation medium are added to an inherent X-ray image, thereby deteriorating the picture quality.

Especially, in an apparatus such as a cone-beam CT apparatus for imaging a three-dimensional distribution of the inside the subject on the basis of a plurality of X-ray images of the subject acquired from many directions around the subject, when blurs are added, in a region where the value of a pixel, that is, the pixel value should be the same, a deviation occurs in the pixel values in each image. Consequently, there are problems such that the picture quality of a three-dimensional image of the inside the subject reconstructed from the X-ray images also deteriorates and the uniformity of the CT number is lowered so that accurate diagnosis cannot be performed. As a method of imaging a three-dimensional distribution of the inside the subject, for example, there is a data correction processing method described in "JAMIT Frontier '95", Medical image engineering research, lecture paper collection, pp. 23–28 (1995)(Literature 6).

There are some known methods of correcting the blur caused by the veiling glare and the blur caused by the scattered X-ray. For example, there is a radiographic apparatus using a method of simultaneously correcting the veiling glare and the scattered X-ray described in "Medical Physics", Vol. 20, pp. 59–69 (1993) (Literature 7). As another method, there is a radiographic apparatus using a method of separately correcting the veiling glare and the scattered X-ray described in "Special Issue of Japan Medial Image Engineering Association Meeting", Vol. 14, No. 4, pp. 383–384 (Literature 8).

SUMMARY OF THE INVENTION

In the direct deconvolution method of the prior art shown in FIG. 3, the two-dimensional Fourier transformation of a measured image is multiplied by a high-pass filter in the spatial frequency space for blur correction, so that a problem arises that high frequency noise such as aliasing noise due to the image component at a frequency higher than the Nyquist frequency decided by the sampling pitch of a digital image is emphasized.

In the blurred image formation method of the prior art shown in FIG. 4, the two-dimensional Fourier transformation of a measured image is multiplied by a low-pass filter in the spatial frequency space, so that the high frequency noise is not increased in the spatial frequency space. However, a point spread function of veiling glare and scattered X-ray which are integrated is used, so that a problem arises that veiling glare and scattered X-ray cannot be corrected precisely. Namely, the point spread function of veiling glare is decided by the size of view field but does not depend on the X-ray tube voltage, anti-scatter grid, and thickness of subject.

However, the point spread function of scattered X-ray depends on, unlike the point spread function of veiling glare, not only the size of view field but also the X-ray tube voltage, anti-scatter grid, and thickness of subject. Therefore, a problem arises that for a subject in which the range of thickness is large, the correction based on the blurred image formation method of the prior art is extremely approximate.

In the prior art, a problem arises that a halation in which the effect of scattered X-ray and veiling glare is relatively excessive is not taken into account in the peripheral area of the area where a light of excessive intensity enters into an imaging device and the output of the imaging device reaches the saturation level, and when halation occurs, the correction becomes insufficient.

Furthermore, in the prior art, a process of correcting the veiling glare component and the scattered X-ray component individually at high speed for fluorographic images which are measured continuously cannot be performed.

In the conventional radiographic apparatus shown in the above-mentioned literatures 6 and 7 intensity distribution functions of the veiling glare and the scattered X-ray, that is, a veiling glare filter and a scattered X-ray filter are obtained and a two-dimensional convolution operation of the filters and a measured image is performed. Consequently, the construction of the operating part is complicated and a load required for the operation is large, so that there is a problem that the blurs caused by the veiling glare and the scattered X-ray cannot be corrected at high speed.

Especially, in an apparatus such as the cone-beam CT apparatus described in Literature 1 for imaging the three-dimensional distribution of the inside the subject on the basis of the plurality of X-ray images of the subject acquired from many directions around the subject, there is a problem that the image correction takes more time as compared with general X-ray fluoroscopy and radiography since a process for correcting many X-ray images has to be performed.

That is, as shown in FIG. 23, as a veiling glare filter 2302 and a scattered X-ray filter 2307, those measured data by a point spread function or a line spread function preliminarily obtained by measurement or functions obtained by fitting a Gauss function or an exponential function are used. Since each of the functions has generally a shape having a wide bottom, when the functions are used as filters, there is a problem that an operation amount of the convolution in each of steps 2303 and 2308 for obtaining a veiling glare component image 2304 and a scattered X-ray component image 2309 is enormous, so that the correction process cannot be performed at high speed. On the other hand, there is a problem such that, in order to execute the process, a special operating means which can execute the Fourier transformation is necessary.

An object of the present invention is to provide a method of X-ray image generation and apparatus thereof for precisely correcting a blur of an X-ray image caused by veiling glare and scattered X-ray for a fluorographic image or radiographic image.

Another object of the present invention is to provide a method of X-ray image generation and apparatus thereof for deciding a veiling glare intensity distribution function and a scattered X-ray intensity distribution function which are necessary for the aforementioned correction by a brief method.

Still Another object of the present invention is to provide a method of X-ray image generation and apparatus thereof for executing the aforementioned correction approximately even if the output of an imaging device is saturated and halation occurs.

A further object of the present invention is to provide a method of X-ray image generation and apparatus thereof for executing the aforementioned correction at high speed without using a special processor. A still further object of the present invention is to provide a method of X-ray image generation and apparatus thereof for correcting a blur approximately for a fluorographic image changing continuously.

A further object of the present invention is to provide a radiographic apparatus which can improve the image quality of an X-ray fluoroscopic image or an X-ray radiographic image at high speed Another object of the invention is to provide a radiographic apparatus which can correct at high speed a blur caused by the scattered X-ray in the X-ray fluoroscopic image or the X-ray radiographic image.

Further another object of the invention is to provide a radiographic apparatus which can correct at high speed a blur caused by the veiling glare in the X-ray fluoroscopic image or the X-ray radiographic image.

Further another object of the invention is to provide a radiographic apparatus which can improve the image quality of a three-dimensional reconstructed image obtained by a three-dimension reconstruction.

Further another object of the invention is to provide a radiographic apparatus which can improve the uniformity of a CT number of a three-dimensional reconstructed image obtained by a three-dimensional reconstruction.

The first object of the present invention is accomplished by the constitution shown in FIG. 1B. A veiling glare intensity distribution function is obtained from the product of the obtained veiling glare intensity ratio and the obtained point spread function of veiling glare, and an image of veiling glare component is calculated from a convolution of the veiling glare intensity distribution function and a measured image.

An image of scattered X-ray component is calculated from a convolution of a scattered X-ray intensity distribution function, obtained from the product of the scattered X-ray intensity ratio obtained from a measured image and the imaging condition of the measured image and the point spread function of scattered X-ray obtained beforehand, and the measured image. A corrected image is obtained by subtracting a veiling glare component image and a scattered X-ray component image from the measured image. The degradation model will be explained by referring to FIG. 1A. In the degradation model shown in FIG. 1A, by a convolution 405 of a product 404 (hereinafter abbreviated to "scattered X-ray intensity distribution function") of a scattered X-ray intensity ratio $a_s$ 402 and a point spread function of scattered X-ray $PSF_s$ 403 and of an ideal image $I_p$ 401, a scattered X-ray component image $I_s$ 406 is generated by Formula (1). In the following description, a symbol ** indicates a two-dimensional convolution and a symbol * indicates a one-dimensional convolution.

The point spread function is normalized so that the integral value becomes 1.

$$I_s = a_s \cdot I_p ** PSFs \qquad (1)$$

By addition 407 of the scattered X-ray component image $I_s$ and the ideal image $I_p$, a blurred image by scattered X-ray 408 is generated. A product 411 (hereinafter abbreviated to "veiling glare intensity distribution function") is made of a veiling glare intensity ratio $a_v$ 409 and a point spread function of veiling glare $PSF_v$ 410. By a convolution 421 of the product 411 and the blurred image 408, a veiling glare component image 413 is generated by Formula (2).

$$I_v = a_v \cdot (I_p + I_s) ** PSF_v \qquad (2)$$

By addition 414 of $I_v$ and $I_s$ to $I_p$, a measured image $I_t$ 415 is generated from Formula (3).

$$I_t = I_p + I_s + I_v \qquad (3)$$

Next, the correction process on the basis of the aforementioned degradation model will be explained. The correction process is expressed by Formula (4) to Formula (6) by Formula (1) to Formula (3). Formula (7) to Formula (9) are obtained by solving Formula (4) to Formula (6). The correction process is performed by using these formulas.

FIG. 1B shows a flow chart of the correction process. A veiling glare intensity distribution function is obtained as the product 411 of the veiling glare intensity ratio 409 obtained beforehand and the point spread function of veiling glare 410 obtained beforehand. A veiling glare component image $I_v$ 418 is calculated by a deconvolution 417 of the veiling glare intensity distribution function and the measured image 415 (Formula (7)). The scattered X-ray intensity distribution function is obtained as the product 404 of the scattered X-ray intensity ratio 402, which is obtained from the measured image 415 the imaging condition of the measured image, and the point spread function of scattered X-ray 403. A scattered X-ray component image $I_s$ 420 is calculated by a deconvolution 419 of the scattered X-ray intensity distribution function and the measured image 415 (Formula (8)). A corrected image $I_p$ 422 is obtained by subtracting 421 the veiling glare component image 418 and the scattered X-ray component image 420 from the measured image 415 (Formula (9)).

$$I_v = a_v \cdot (I_t - I_v)^{**} PSF_v \quad (4)$$

$$I_s = a_s \cdot (I_t - I_v - I_s)^{**} PSF_s \quad (5)$$

$$I_p = I_t - I_v - I_s \quad (6)$$

Hereinafter, F2[ ] indicates a two-dimensional Fourier transformation and FR2{ } indicates a two-dimensional inverse Fourier transformation.

$$I_v = FR2\{F2[I_t] \cdot \{a_v \cdot F2[PSF_v]\}/(1 + a_v \cdot F2[PSF_v])\} \quad (7)$$

$$I_s = FR2\{F2[I_t] \cdot \{a_s \cdot F2[PSF_s]\}/(1 + a_s \cdot F2[PSF_s])\} \cdot \{1/(1 + a_v \cdot F2[PSF_v])\} \quad (8)$$

$$I_p = I_t - FR2\{F2[I_t] \cdot \{(a_v \cdot F2[PSF_v])/(1 + a_v \cdot F2[PSF_v])\}\} - FR2\{F2[I_t] \cdot \{(a_s \cdot F2[PSF_s])/(1 + a_s \cdot F2[PSF_s])\} \cdot \{1/(1 a_v \cdot F2[PSF_v])\} \quad (9)$$

The filters in the spatial frequency space are $\}a_v \cdot F2[PSF_v])/(1 + a_v \cdot F2]PSF_v]\}$ on the right side of Formula (7) and $\{a_s \cdot F2[PSF_s])/(1 + a_s \cdot F2[PSF_s])\} \cdot \{1/(1 + a_v \cdot F2[PSF_v])\}$ on the right side of Formula (8), and both of them approach zero in the high frequency area. Therefore, these filters are not high-pass filters but low-pass filters and the high frequency noise is not emphasized by operations in the spatial frequency space.

The second object of the present invention is accomplished by the following constitution. An edge spread image when there is no subject is measured in each of the vertical and horizontal directions of a matrix in which pixels of a measured image are arranged.

This edge spread image is differentiated, and a line spread image when there is no subject is obtained, and this line spread image is fit by two functional components. The wider spread component among the two components is assumed as a veiling glare component, and the intensity ratio and the line spread function of this veiling glare component is obtained. The product of the line spread functions in the vertical and horizontal directions is assumed as a point spread function of veiling glare component. The average of intensity ratios in the vertical and horizontal directions is assumed as an intensity ratio of veiling glare component. The product of the point spread function of veiling glare component and the intensity ratio of veiling glare component is assumed as a veiling glare intensity distribution.

Furthermore, edge spread images obtained when phantoms whose X-ray absorption coefficients are similar to that of human body having a uniform thickness (for example, an acrylic plate) are measured. A one-dimensional veiling glare image is obtained by using the one-dimensional convolution or the one-dimensional Fourier transformation of the edge spread image and the product which is made of the line spread function of veiling glare and the intensity ratio of veiling glare component. A veiling glare correction is executed by subtracting the one-dimensional veiling glare image from the edge spread image. A veiling glare correction line spread image for the corresponding subject thickness is obtained by differentiating the corrected image, and the veiling glare correction line spread image is fit by two functional components.

The wider spread component among the two components is assumed as a scattered X-ray component, and the line spread function and the intensity ratio of this scattered X-ray component are obtained. The product of the line spread functions in the vertical and horizontal directions is assumed as a point spread function of scattered X-ray component, and the average of intensity ratios in the vertical and horizontal directions is assumed as an intensity ratio of scattered X-ray. The product of the point spread function of scattered X-ray component and the intensity ratio of scattered X-ray component is assumed as a scattered X-ray intensity distribution.

The third object of the present invention is accomplished by the following constitution. As shown in FIG. 5, a discrimination operation for whether a measured image (fluorographic image of radiographic image) (501) includes a saturation value is performed (502). When it includes a saturation value, the saturation level is corrected by exchanging the saturated pixel value (504) to a value estimated from other measured value around the same position (503) and both the veiling glare and scattered X-ray are corrected after saturation level correction (505). When the output of an imaging device is saturated and halation occurs, both the veiling glare and scattered X-ray are corrected approximately in this way.

The fourth object of the present invention is accomplished by the following constitution. A sampled measured image and a sampled veiling glare distribution or a sampled scattered X-ray distribution, in which the matrix size of each data is reduced by discretely sampling, are obtained. A convolution of the sampled measured image and the sampled veiling glare distribution or a convolution of the sampled measured image and the sampled scattered X-ray distribution is executed, and the matrix size of the image resulted from convolution is returned to the original size by performing an image magnification process using the interpolation method The image returned to the original matrix size is subtracted from the measured image.

The fifth object of the present invention is accomplished by the following constitution. Veiling glare component images and scattered X-ray component images are calculated using fluorographic images sampled intermittently from fluorographic images continuously acquired. When these calculated components are to be subtracted from fluorographic images, they are subtracted from the latest fluorographic image to be displayed next instead of the original fluorographic images sampled intermittently.

According to the method of X-ray image generation and apparatus thereof of the present invention, correction of a blur of an X-ray image caused by a veiling glare and scattered X-ray is executed precisely for a fluorographic image or a radiographic image by using the point spread function of veiling glare and the point spread function of scattered X-ray without the high frequency noise being emphasized, and a blur can be corrected with high precision also for a subject having a wide range of thickness. A veiling glare spread function and a scattered X-ray spread function necessary for the aforementioned correction can be decided by a brief method. Even when the output of an imaging device is saturated and halation occurs, the aforementioned correction can be executed approximately.

The aforementioned correction can be executed at high speed without using a special processor and can be applied also to fluorography, radiography of an extremely fine image (for example, comprising 2000×2000 pixels or 4000×4000 pixels), and cone beam CT (for example, 240 images of 512×512 pixels are picked up for 4.8 seconds) which require high speed processing. Furthermore, even when the time required for the correction process is longer than the time of one frame of fluorography image, blur correction can be executed approximately for fluorographic images changing continuously.

DETAILED DESCRIPTION OF THE PREFERRED EMBODIMENTS

Embodiment 1

Figure 1A:
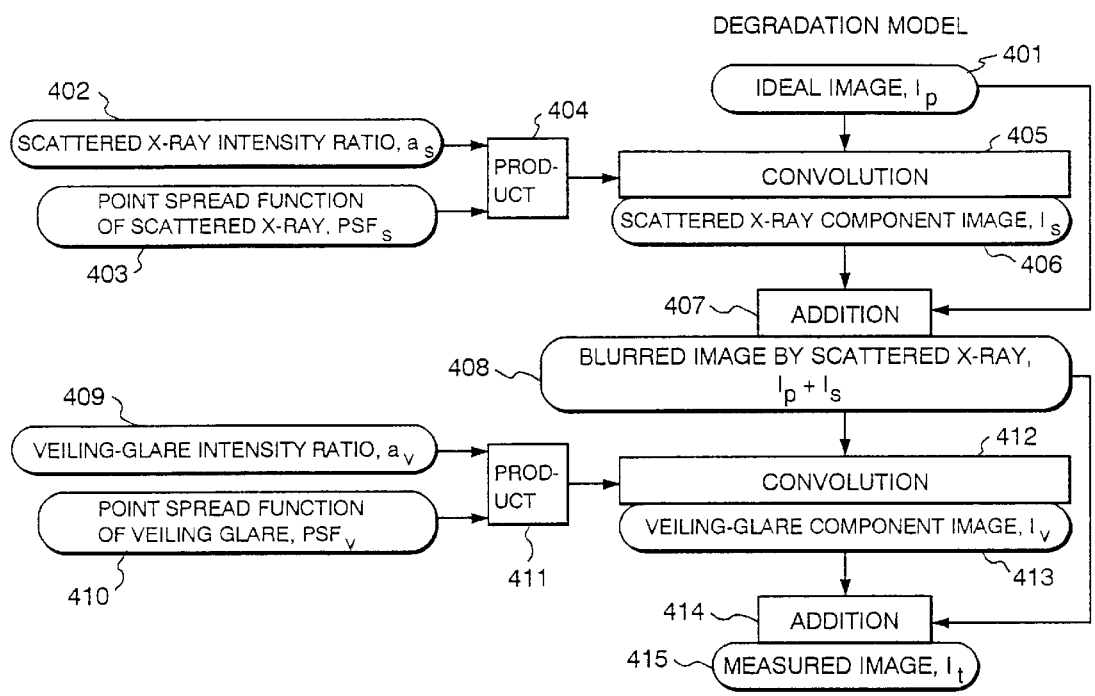
FIGS. 1A and 1B are schematic flow charts showing a degradation model and correction process of the present invention.
Figure 1B:
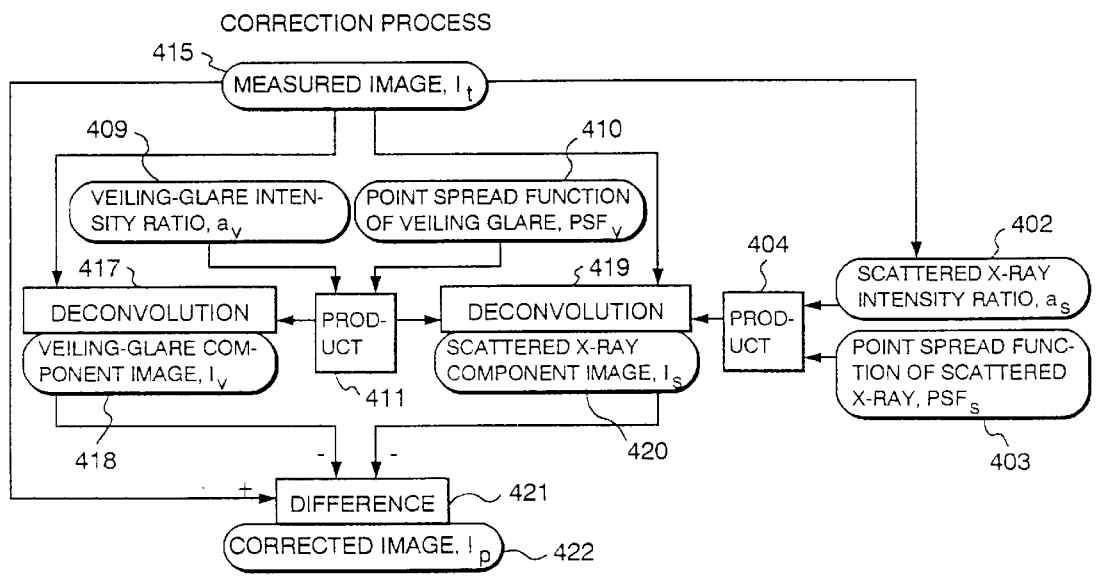
Figure 2:
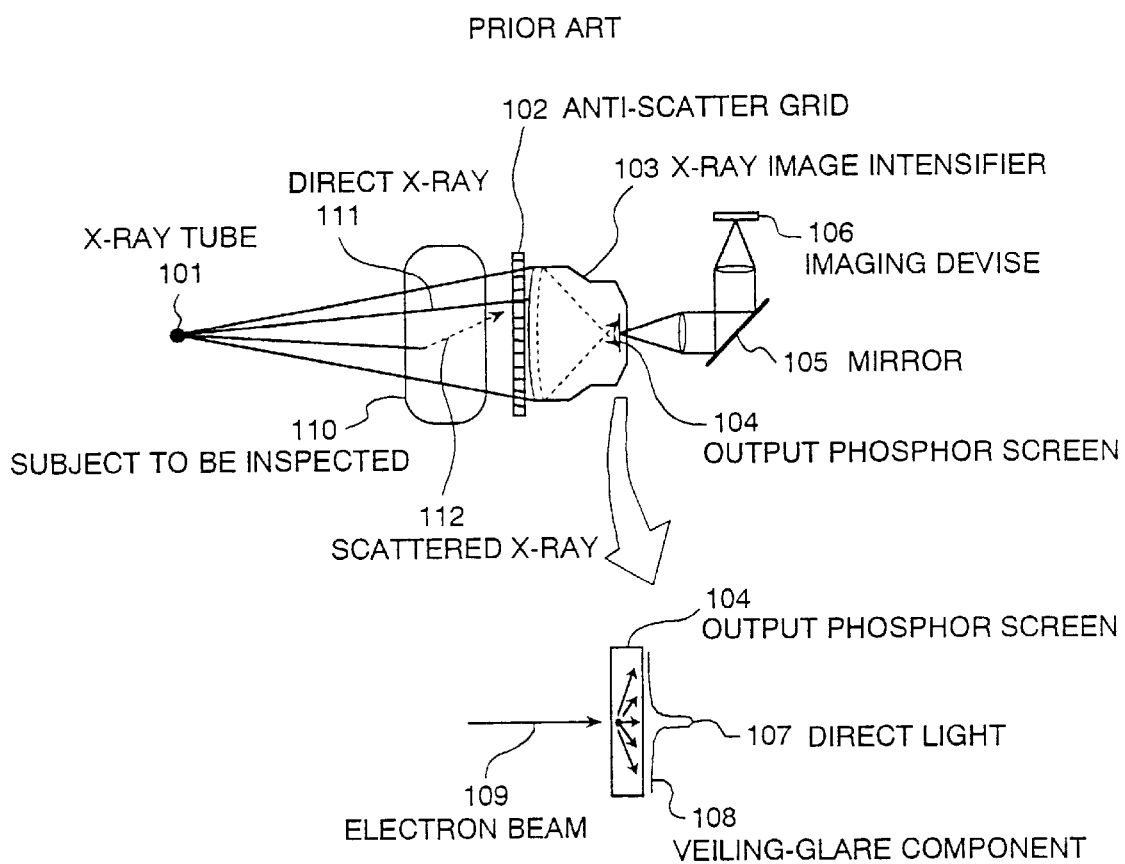
FIG. 2 is a constitution diagram of a typical example of an X-ray detection system by the conventional method which is used in the present invention.
Figure 3A:
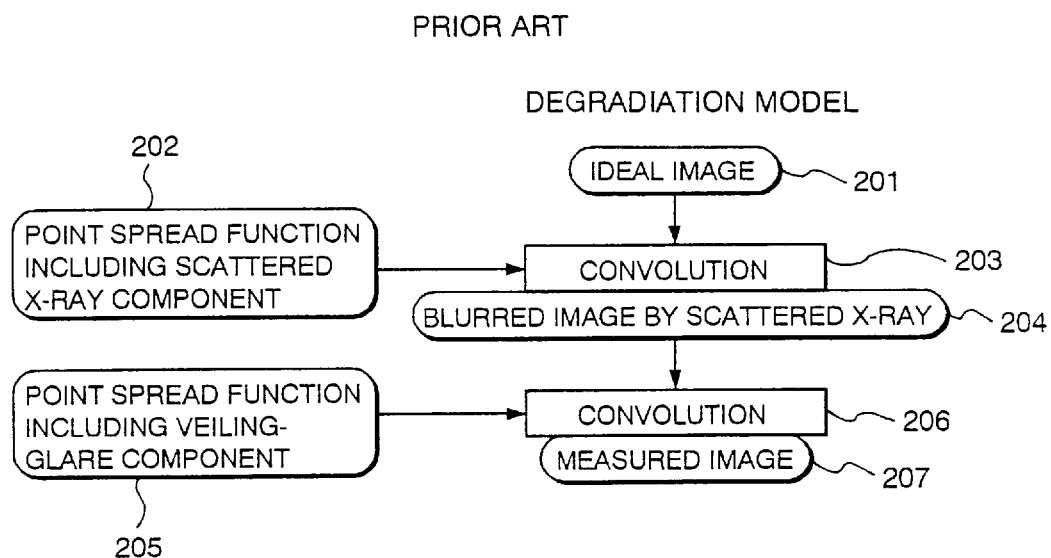
FIG. 3A is a flow chart showing an example of degradation model by the conventional method.
Figure 3B:
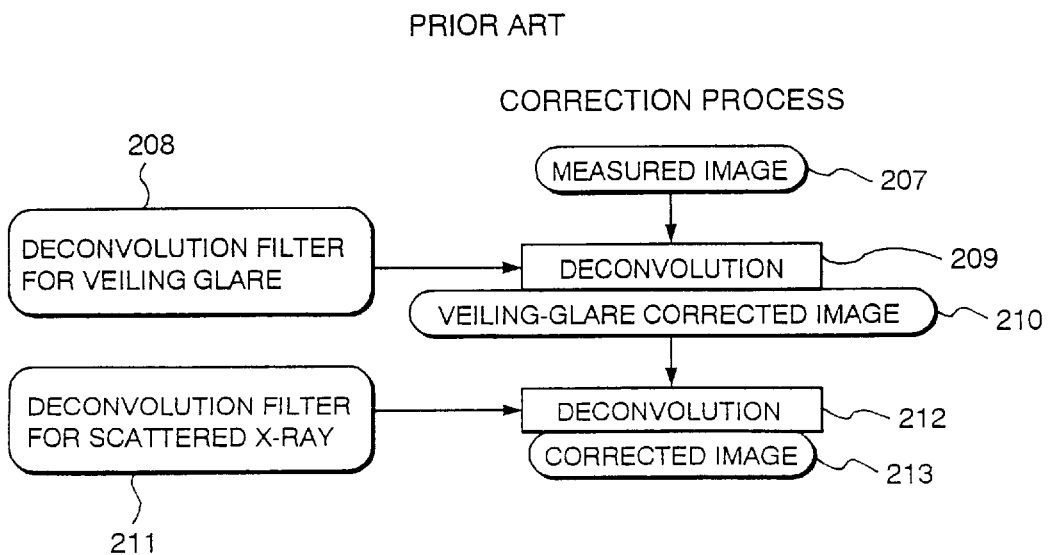
FIG. 3B is a flow chart showing an example of correction process by the conventional method.
Figure 4A:
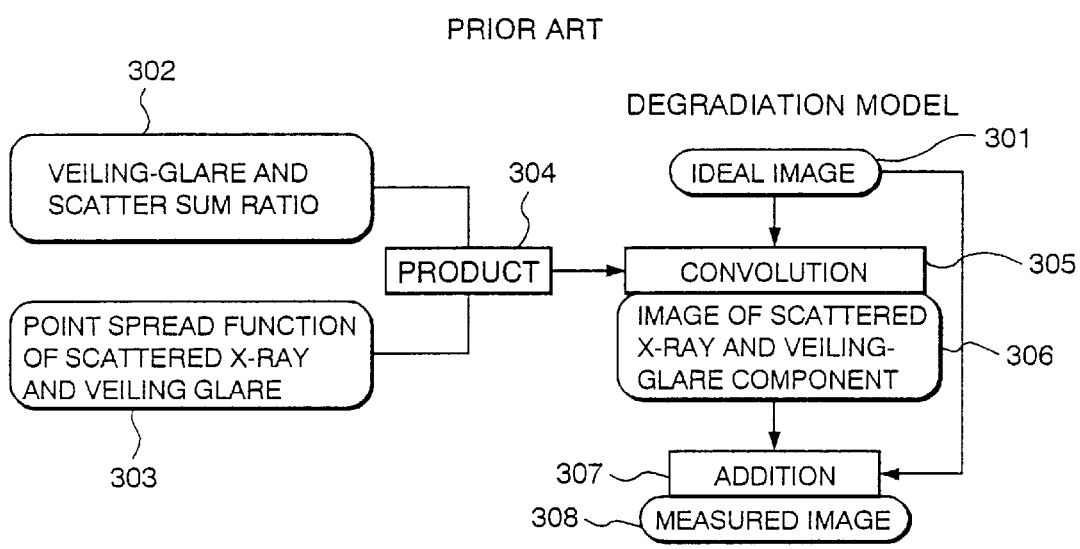
FIG. 4A is a flow chart showing another example of degradation model by the conventional method.
Figure 4B:
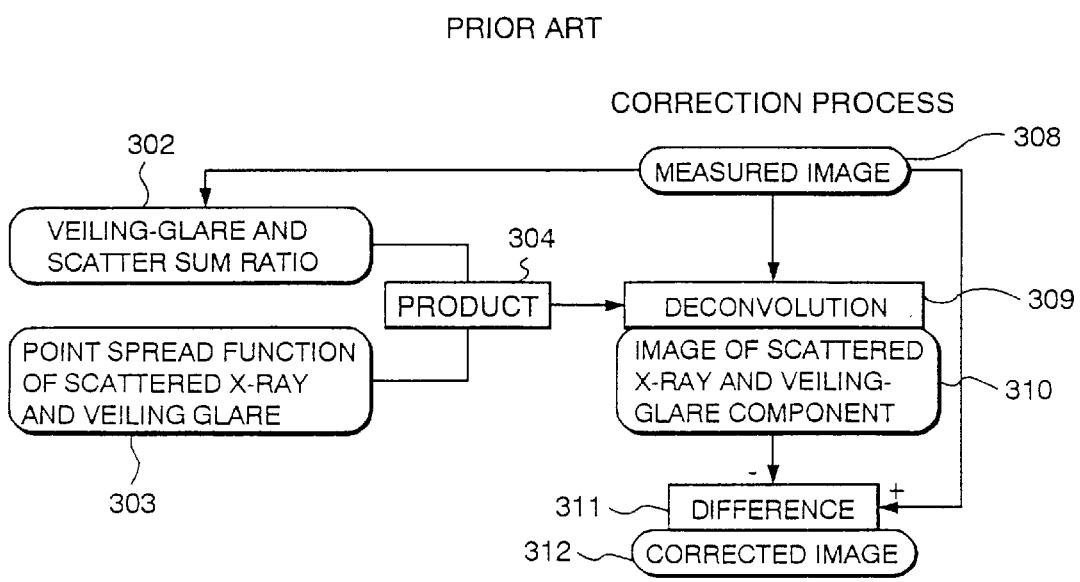
FIG. 4B is a flow chart showing another example of correction process by the conventional method.
Figure 5:
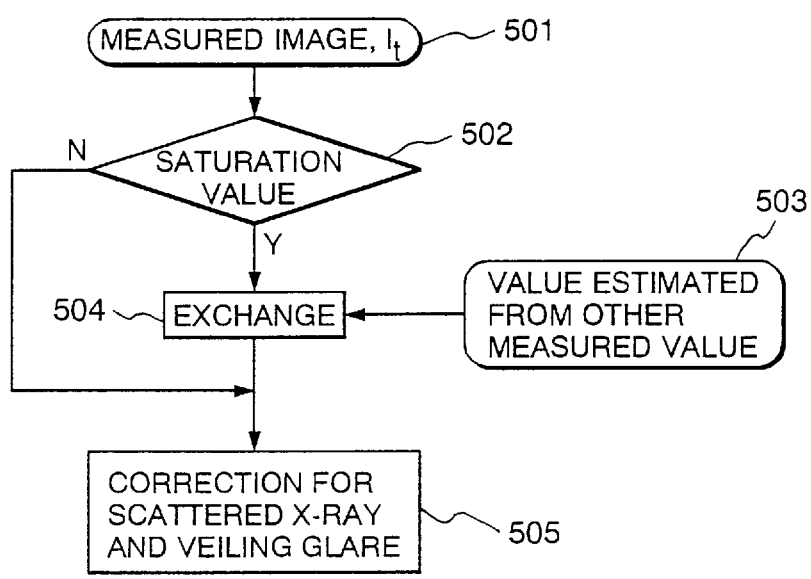
FIG. 5 is a flow chart showing approximate correction when saturation occurs in the present invention.
Figure 6:
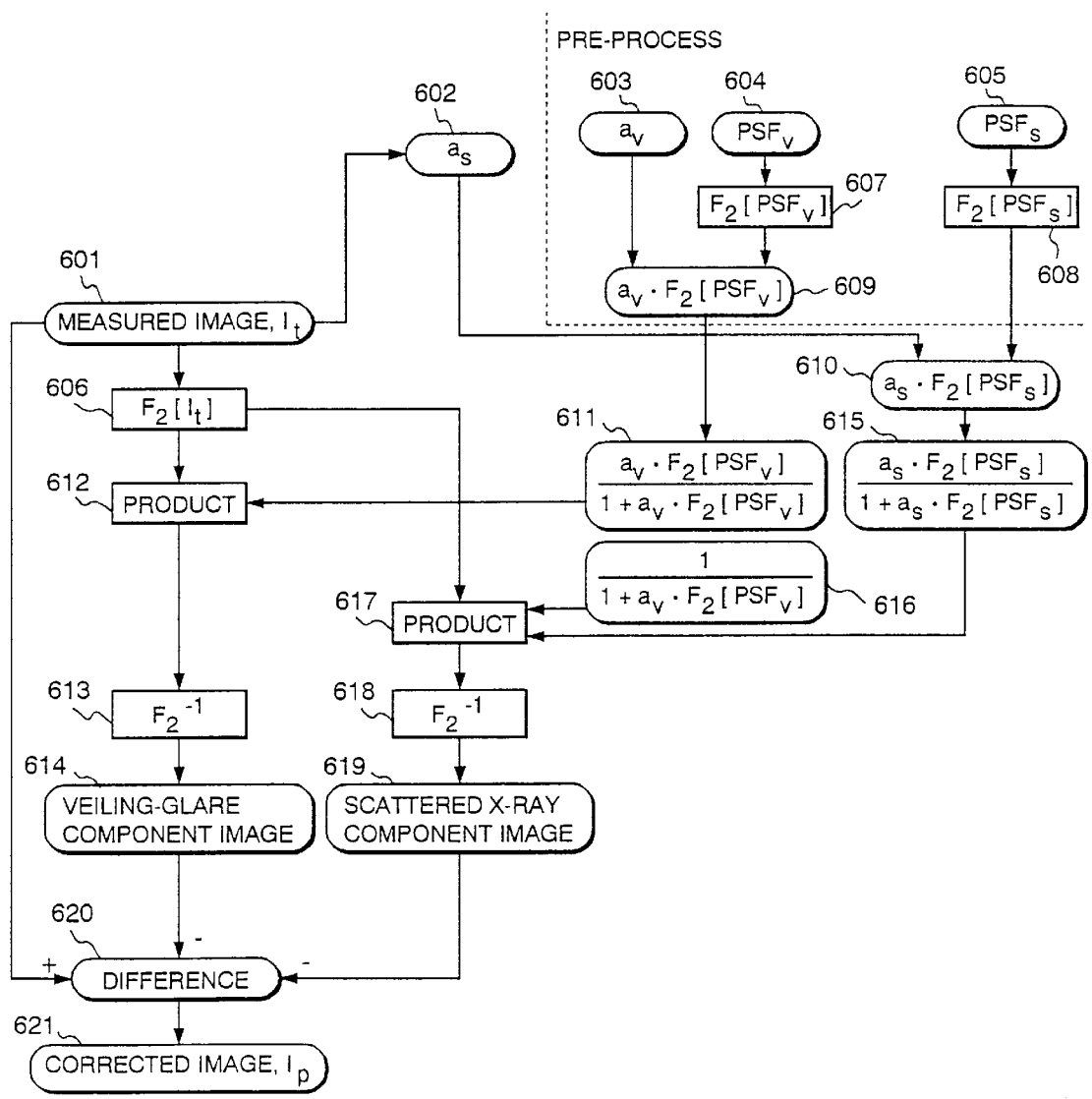
FIG. 6 is a flow chart showing the correction process using the Fourier transformation method in the first embodiment of the present invention.

FIG. 6 is a block diagram showing an embodiment of the X-ray image formation method of the present invention. Firstly, two-dimensional Fourier transformations 606, 607, and 608 of a measured image $I_t$ 601 comprising a fluorographic image or a radiographic image, a point spread function of veiling glare $PSF_v$ 604, and a point spread function of scattered X-ray $PSF_s$ 605. From the product of a veiling glare intensity ratio $a_v$ 603 and the two-dimensional Fourier transformation 607 of the point spread function of veiling glare $PSF_v$ 604, a two-dimensional Fourier transformation image 609 of the veiling glare distribution function is obtained.

A two-dimensional Fourier transformation image is an image in which a frequency is taken in the horizontal and vertical directions respectively and each pixel value expresses the intensity at a certain frequency. The two-dimensional Fourier transformation image 609 is divided by an image in which 1 is added to the two-dimensional Fourier transformation image 609, and a result of the division 611 is multiplied by the two-dimensional Fourier transformation image 606 of the measured image, and a result of the multiplication 612 is subjected to a two-dimensional inverse Fourier transformation 613, and a veiling glare component image 614 is calculated (Formula (7)).

A scattered X-ray intensity ratio $a_s$ 602 is obtained from the measured image $I_t$ and the measurement condition. An actual example of the method will be described later in detail. From the product of the scattered X-ray intensity ratio $a_s$ 602 and the two-dimensional Fourier transformation 608 of the point spread function of scattered X-ray $PSF_s$ 605, a two-dimensional Fourier transformation image 610 of the scattered X-ray distribution function is obtained.

The two-dimensional Fourier transformation image of the scattered X-ray distribution function is divided by an image in which 1 is added to the two-dimensional Fourier transformation image of the scattered X-ray distribution function, and a result of the division 615 is multiplied by a reciprocal 616 of the result that 1 is added to the two-dimensional Fourier transformation image of the veiling glare distribution function, and a result of the multiplication is multiplied by the two-dimensional Fourier transformation image 606 of the measured image $I_t$. Furthermore, a result of the multiplication 617 is subjected to a two-dimensional inverse Fourier transformation 618 and a scattered X-ray component image 619 is calculated (Formula (8)).

The veiling glare component image 614 and the scattered X-ray component image 619 are subtracted form the measured image 601 (Formulas (6) and (620)). By this process, a target image 621 in which both the veiling glare component and scattered X-ray component contained in the measured image $I_t$ are corrected is obtained Embodiment 2

Figure 7:
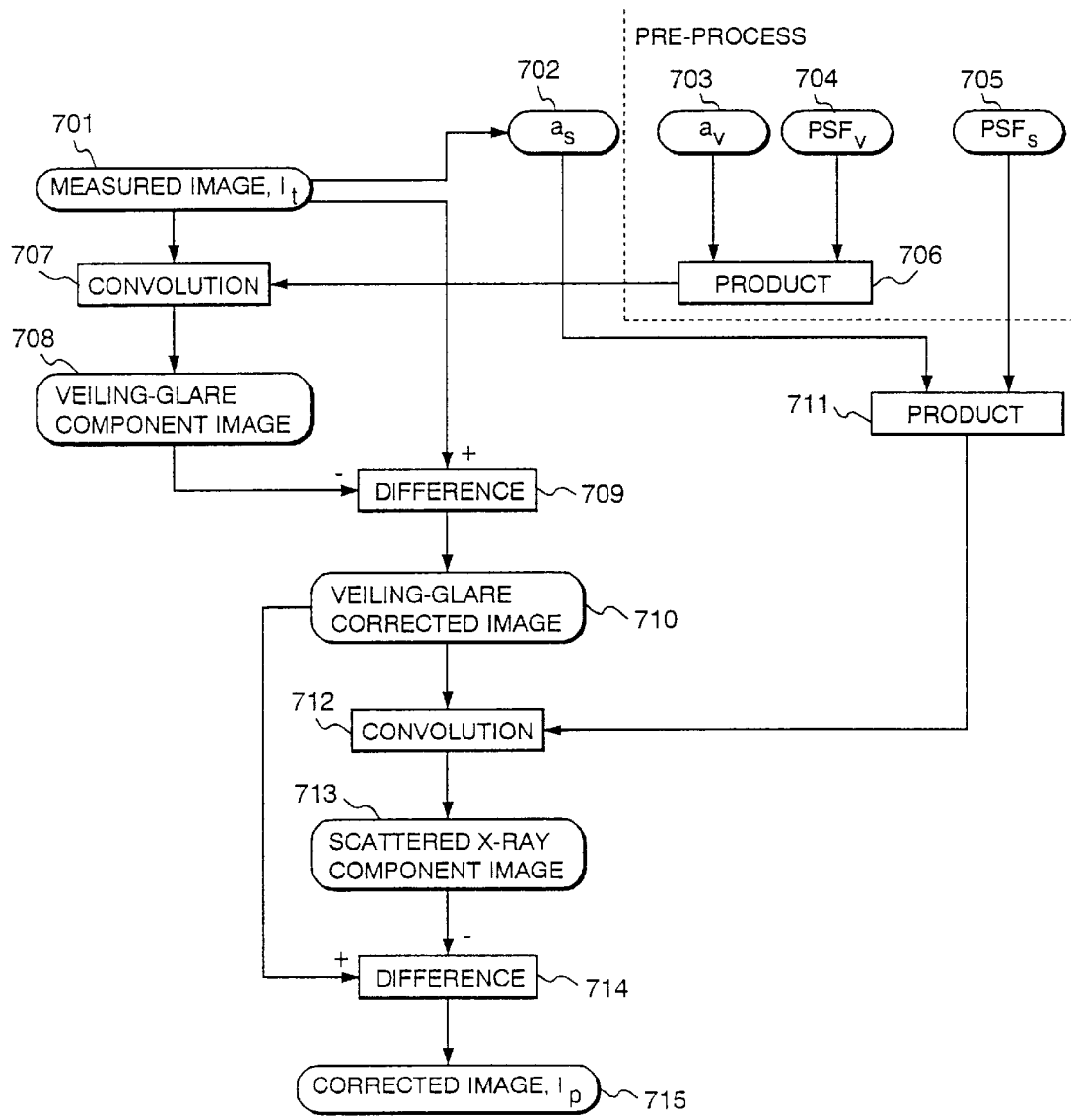
FIG. 7 is a flow chart showing the correction process using the convolution method in the second embodiment of the present invention.

FIG. 7 is a block diagram showing another embodiment of the X-ray image formation method of the present invention. This embodiment is different from Embodiment 1 in a point that an image is corrected using a two-dimensional convolution instead of a two-dimensional Fourier transformation.

Firstly, the principle will be explained. A true veiling glare component image $I_v$ by the convolution method is expressed by Formula (10) obtained by substituting Formula (4) repeatedly for $I_v$ of the right side of Formula (4).

$$I_v = a_v \cdot I_t  PSF_v - a_v^2 \cdot I_t  PSF_v  PSF_v + a_v^3 \cdot I_t  PSF_v  PSF_v  PSF_v \quad (10)$$

A true scattered X-ray image is expressed by Formula (11) obtained by substituting Formula (5) repeatedly for $I_s$ of the right side of Formula (5).

$$I_s = a_s \cdot (I_t - I_v)  PSF_s - a_s^2 \cdot (I_t - I_v)  PSF_s  PSF_s + a_s^3 \cdot (I_t - I_v)  PSF_s  PSF_s  PSF_s \quad (11)$$

Therefore, a corrected image $I_p$ is obtained by substituting Formula (10) and Formula (11) for Formula (6).

A method for correcting an image by an approximate formula will be explained hereunder. Taking up that $a_v$ is smaller than 1, Formula (12) is obtained by expressing an approximate veiling glare component image $I_v'$ by the first term of Formula (10).

$$I_v' = a_v \cdot I_t ** PSF_v \quad (12)$$

Taking up that $a_s$ when an anti-scatter grid is used is generally smaller than 1, an approximate scattered X-ray component image $I_s'$ is expressed by the first term of Formula (11). Furthermore, Formula (13) is obtained by approximating $I_v$ to $I_v'$.

$$I_s' = a_s \cdot (I_t - I_v') ** PSF_s \quad (13)$$

An approximate corrected image P' is obtained from Formula (14) using Formulas (6), (12), and (13).

$$I_p' = I_t - I_v' - I_s' \quad (14)$$

A correction error e of the corrected image P' is expressed by a difference ($e = I_p' - I_p$) between $I_p'$ in Formula (14) and $I_p$ mentioned above. The correction error is a term of second or higher degree of $a_v$ and $a_s$ and since $a_v$ and $a_s$ are generally smaller than 1, an image can be corrected approximately. When it is necessary to increase the accuracy of approximation, it is desirable to obtain the first and second terms mentioned above by processing and add them to the corrected image.

FIG. 7 is a flow chart showing the process explained above concretely. Firstly, before obtaining a measured image $I_t$ 701, a veiling glare distribution function 706 is obtained from the product of a veiling glare intensity ratio $a_v$ 703 and a point spread function of veiling glare $PSF_v$ 704. A scattered X-ray intensity ratio $a_s$ 702 is obtained from the measured image and measurement condition. An actual example of the method will be described later. A scattered X-ray distribution function 711 is obtained from the product of the scattered X-ray intensity ratio $a_s$ 702 and a point spread function of scattered X-ray $PSF_s$ 705. The veiling glare distribution function 706 is convoluted (707) for the measured image $I_t$ 701 and a veiling glare component image $I_v'$ 708 is calculated (Formula (12)).

The veiling glare component image $I_v'$ 708 is subtracted (709) from the measured image $I_t$ 701 and a veiling glare corrected image $I_q'$ 710 is calculated. A scattered X-ray distribution function 711 is convoluted (712) for the veiling glare corrected image $I_q'$ 710 and a scattered X-ray component image $I_s'$ 713 is calculated (Formula (13)). The scattered X-ray component image $I_s'$ 713 is subtracted (Formula (14)) (714) from the veiling glare corrected image $I_q'$ 710 and an image $I_p'$ 715 in which both the veiling glare component $I_v'$ and the scattered X-ray component $I_s$ contained in the measured image $I_t$ are corrected is obtained.

Embodiment 3

Figure 8:
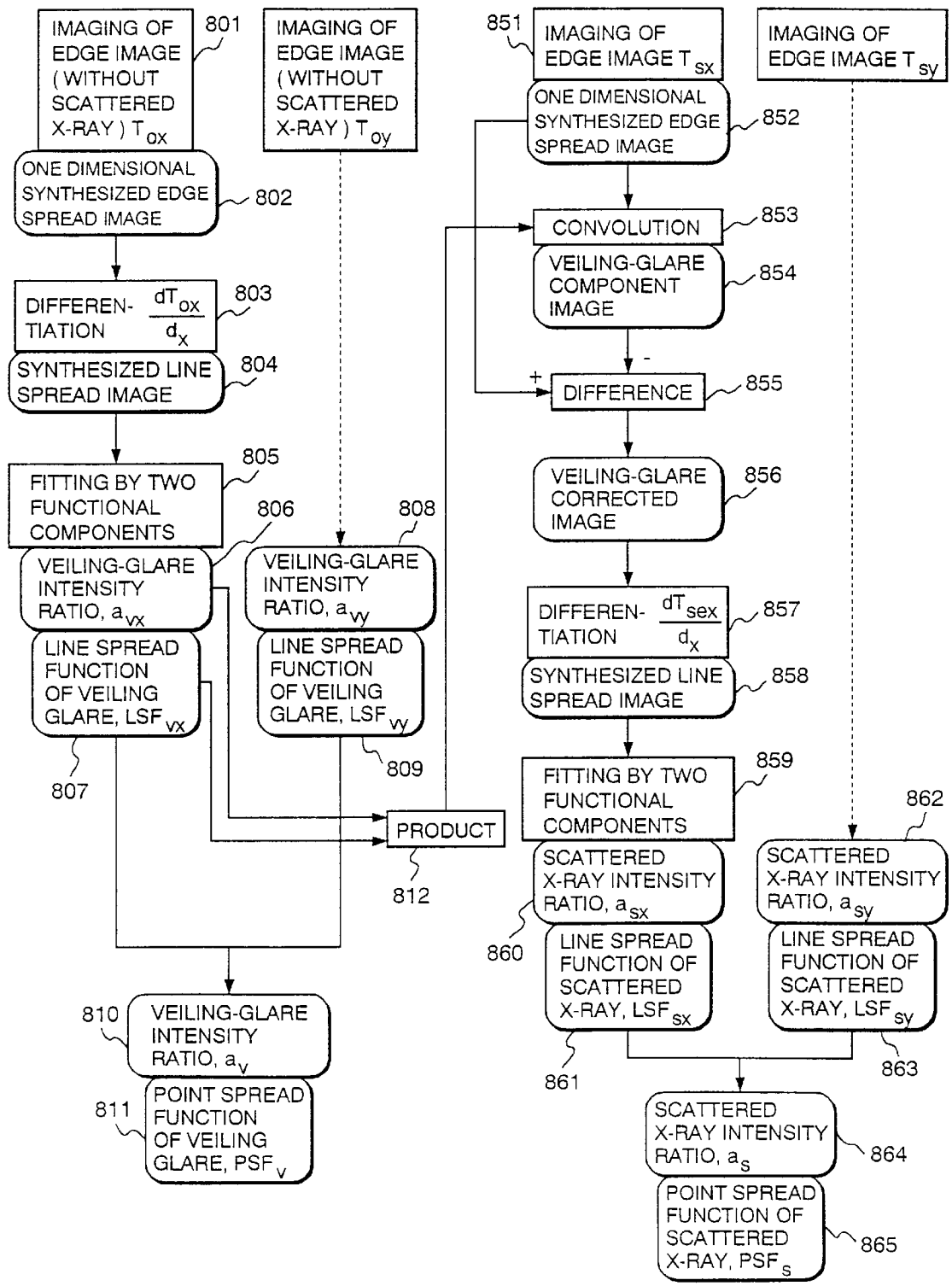
FIG. 8 is a flow chart for obtaining veiling glare and scattered X-ray intensity ratios and a point spread functions of the present invention.
Figure 9A:
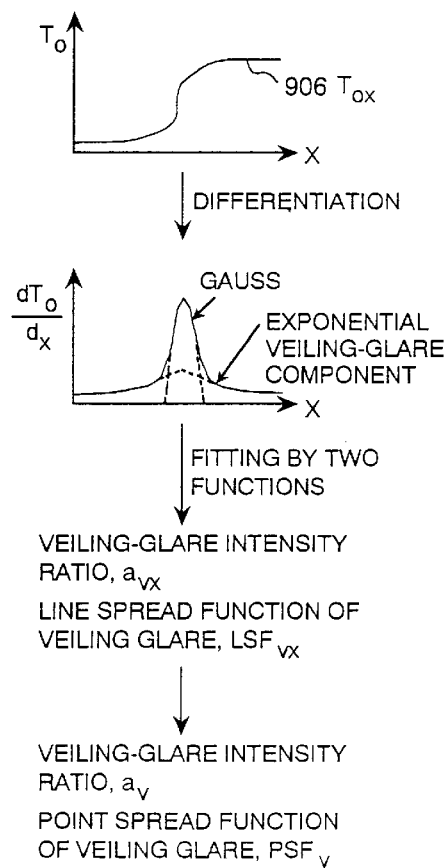
FIGS. 9A and 9B are drawings for obtaining veiling glare and scattered X-ray intensity ratios and a point spread functions of the present invention.

Next, a method for obtaining the veiling glare intensity ratio $a_v$ and the point spread function of veiling glare $PSF_v$ by measurement will be explained by referring to FIGS. 8, 9A, and 9B. FIG. 9A shows a measurement system for measuring the veiling glare intensity ratio and the veiling glare edge distribution function, the rough shape of a measured edge image, and the rough shape of a differentiated edge image. An edge 903 of a metallic plate 902 is arranged at the center of the field of view at a distance of about 25 cm from a grid 904 so that it intersects the X axis orthogonally.

A scattering medium is not arranged and an edge measured image $T_{ox}$ is measured (801). A blur is added to the measured edge image due to a veiling glare. Next, a differentiated image of the measured edge image is obtained (803). In the differentiated edge image, the Gauss curve indicates a resolution of the detector and the exponential curve indicates a distribution of light diffusion. The differentiated edge image is fit by two functional components 805 and a veiling glare intensity ratio ax 806 and a line spread function $LSF_{vx}$ 807 are obtained. The method will be described hereunder in detail. The rough shape of the measured edge image is shown by a curve 906. The measured edge image $T_{ox}$ includes no scattered X-ray component, so that it is expressed by Formula (15) using Formula (3).

$$T_{ox} = P_{ox} + V_{ox} \quad (15)$$

Assuming that $a_{pox}$ is a term proportional to the intensity of direct X-rays during measurement and $PSF_{px}$ is a point spread function of a direct X-ray image, the direct X-ray component image $P_{ox}$ is expressed by Formula (16).

$$P_{ox} = a_{pox} \cdot ESF_{px} \quad (16)$$

Assuming that the measured veiling glare component intensity ratio is $a_{vx}$ and $ESF_{vx}$ is a veiling glare edge distribution function, the veiling glare component image $V_{ox}$ is expressed by Formula (17).

$$V_{ox} = a_{vx} \cdot a_{pox} \cdot ESF_{vx} \quad (17)$$

Therefore, the measured edge image $T_{ox}$ is expressed by Formula (18) using Formulas (15), (16), and (17), and it becomes a function of only x which does not depend on y, and is expressed as linear combination of a two-component edge distribution function (802).

$$T_{ox}=a_{pox} \cdot (ESF_{px}+a_{vx} \cdot ESF_{vx}) \quad (18)$$

Next, a differentiated image of the edge measured image is obtained (803). A differentiated image $d(T_{ox})/dx$ is expressed by Formula (19) using Formula (18).

$$d(T_{ox})/dx=a_{pox} \cdot (LSF_{px}+a_{vx} \cdot LSF_{vx}) \quad (19)$$

$LSF_{px}$ is a line spread function of direct light component and $LSF_{vx}$ is a line spread function of veiling glare component. Namely, the differentiated image $d(T_{ox})/dx$ of the edge measured image is expressed as linear combination of a two-component line spread function (804).

Next, assuming that the line spread function of direct light component $LSF_{px}$ is a normal distribution function (Formula (20)) and the line spread function of veiling glare component $LSF_{vx}$ is an exponential function (Formula (21)), the differentiated image $d(T_{ox})/dx$ is subjected to the fitting by two functional components 805 using the least square method. The veiling glare intensity ratio ax 806 and the line spread function of veiling glare component $LSF_{vx}$ 807 are obtained from Formulas (22) and (23). The differentiated image can be obtained, for example, from the difference between the values of adjacent pixels.

$$a_{pox} \cdot LSF_{px}=a_{1x} \cdot exp(-a_{2x} \cdot x^2) \quad (20)$$

$$a_{pox} \cdot a_{vx} \cdot LSF_{vx}=b_{1x} \cdot exp(-b_{2x} \cdot |x|) \quad (21)$$

$$a_{vx}=(2 \cdot b_{1x}/b_{2x})/\{a_{1x}(/a_{2x})\} \quad (22)$$

$$LSF_{vx}=(b_{2x}/2) \cdot exp(-b_{2x} \cdot |x|) \quad (23)$$

Also in the Y direction, the direction of the edge of the metallic plate is turned in a 90° from the position for measurement in the X direction and arranged at the center of the field of view so that it intersects the Y axis orthogonally, and the measurement and fitting are executed in the same way as in the X direction, and $a_{vy}$ 808 and $LSF_{vy}$ 809 are decided.

The point spread function of veiling glare $PSF_v$ and the veiling glare intensity ratio $a_v$ are obtained from Formulas (24) and (25) (810, 811).

$$PSF_v(x,y)=LSF_{vx}(x) \cdot LSF_{vy}(y) \quad (24)$$

$$a_v=(a_{vx}+a_{vy})/2 \quad (25)$$

When it can be assumed that the characteristics of the X and Y directions are approximately the same, $PSF_v(x,y)$ is expressed by Formula (26) and decided only by $b_2$. However, $b_2=b_{2x}=b_{2y}$.

$$PSF_v(x,y)exp(-b|y|) \quad (26)$$

Figure 9B:
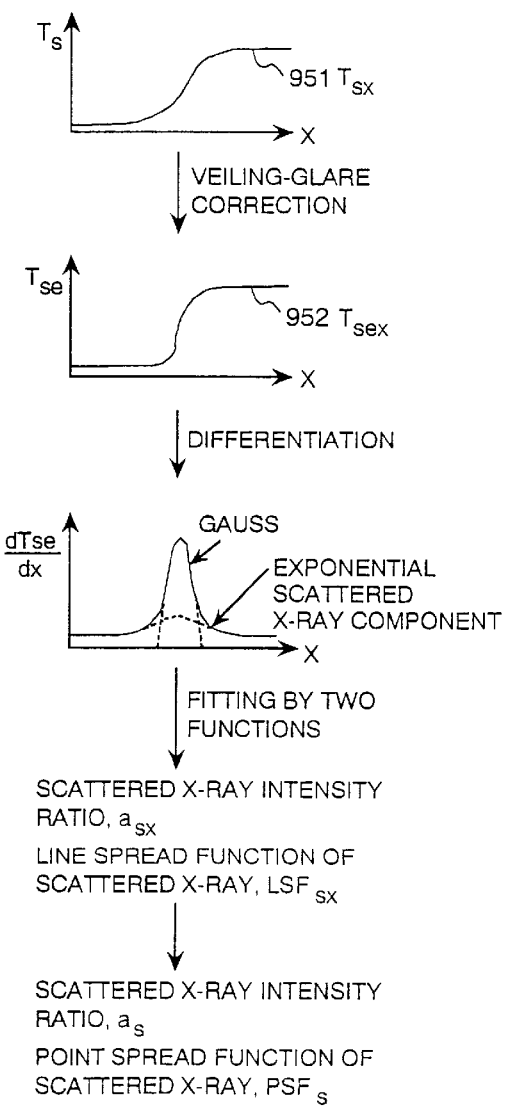

Next, a method for obtaining the scattered X-ray intensity ratio $a_s$ and the point spread function of scattered X-ray $PSF_s$ for a subject having a fixed thickness by way of experiment will be explained FIG. 9B shows a measurement system for measuring the scattered X-ray intensity ratio and the scattered X-ray edge distribution function, the rough shape of a measured edge image, the rough shape of a one-dimensional profile image of a veiling glare corrected image, and a differentiated image. The edge 903 of the metallic plate 902 is arranged at the center of the field of view at a distance of about 25 cm from the grid 904 so that it intersects the X axis orthogonally. As a scattering medium, for example, an acrylic plate is arranged and a measured edge image $T_{sx}$ is measured (851). A blur is added to the edge measured image due to a veiling glare and a scattered X-ray.

Next, the veiling glare component is corrected for this measured edge image using the veiling glare intensity and line spread function of the glare veiling which are obtained previously. A one-dimensional veiling glare component image profile 854 is obtained by one-dimensional convolution 853 for one-dimensional image profile 852 of the measured edge image, and the one-dimensional veiling glare component image profile 854 is subtracted from the one-dimensional profile image 852 (855), and a one-dimensional profile image 856 of a veiling glare corrected image is obtained. Namely, a blur caused by only a scattered X-ray is added to this image 856.

Next, the one-dimensional profile image 856 after the veiling glare correction is differentiated (857) so as to obtain a differentiated image 858. In the differentiated image shown in FIG. 9B, the Gauss curve indicates the resolution of the detector and the exponential curve indicates the distribution of the scattered X-ray. The differentiated image 858 is fit by two functional components, and the scattered X-ray intensity ratio $a_s$ and the line spread function of the scattered X-ray $LSF_s$ are obtained, and then the point intensity spread function is obtained from it. This method will be described in detail hereunder.

The measured edge image $T_{sx}$ includes the scattered X-ray component and is expressed by Formula (27) using Formula (3).

$$T_{sx}=P_s+V_s+S_s \quad (27)$$

where $P_s$ indicates a direct X-ray component image, and $V_s$ indicates a veiling glare component image, and $S_s$ indicates a scattered X-ray component image. Each of these component images becomes a function of only x which does not depend on y and the images are expressed by Formulas (28), (29), and (30) respectively $$Ps=a_{ps} \cdot ESF_{px} \quad (28)$$

$$S_s=a_{ps} \cdot asx \cdot ESF_{sx} \quad (29)$$

$$V_s=a_{ps} \cdot a_{vx} \cdot (ESF_{vx}+asx \cdot (ESF_{sx}**ESF_{vx})) \quad (30)$$

where $a_{ps}$ indicates a term proportional to the intensity of direct X-rays during measurement, and $ESF_{sx}$ indicates an edge distribution function, and $a_{sx}$ indicates a scattered X-ray intensity ratio.

When the veiling glare correction process for $T_{sx}$ is performed by the convolution method, an approximate veiling glare component image $V_{sex}$ (854) is obtained by the process (853) of Formula (31) using $LSF_{vx}$ (807) obtained by Formula (23) and $a_{vx}$ (806) obtained by Formula (22). In Formula (31), a symbol * indicates a one-dimensional convolution.

$$V_{sex}=T_{sx}*(a_{vx} \cdot LSF_{vx}) \quad (31)$$

The veiling glare correction process is performed by Formula (32) using Formulas (27) to (31).

$$T_{sex}=T_{sx}-V_{sex} \quad (32)$$

Next, the differentiated image 857 is obtained as Formula (33) by approximation.

$$d(T_{sex})/dx=a_{ps} \cdot (LSF_{px}+a_{sx} \cdot LSF_{sx}) \quad (33)$$

Namely, the differentiated edge image 857 including a scattered X-ray in which the veiling glare component is corrected is expressed by linear combination of a two-component line spread function (858). $LSF_{sx}$ indicates a line spread function of scattered X-ray component.

Next, assuming that the line spread function of direct X-ray component $LSF_{px}$ is a normal distribution function (Formula (34)) and the line spread function of scattered X-ray component $LSF_{sx}$ is an exponential function (Formula (35)), the differentiated image $d(T_{sex})/dx$ is fit by two functional components (859) using the least square method and a scattered X-ray intensity ratio $a_s$ 860 and a line spread function of scattered X-ray component $LSF_{sx}$ 861 are obtained from Formulas (36) and (37). The differentiated image can be obtained, for example, from the difference between the values of adjacent pixels.

$$a_{ps} \cdot LSF_{px} = a_{3x} \cdot exp(-a_{4x} \cdot x^2) \tag{34}$$

$$a_{ps} \cdot a_{sx} \cdot LSF_{sx} = b_{3x} \cdot exp(-b_{4x} \cdot x^2) \tag{35}$$

$$a_{sx} = (b_{3x}/a_{3x}) \cdot (a_{4x}/b_{4x}) \tag{36}$$

$$LSF_{sx} = (b_{4x}/) \cdot exp(-b_{4x} \cdot x^2) \tag{37}$$

Also in the Y direction, the direction of the edge of the metallic plate is turned a 90° from the position for measurement in the X direction and arranged at the center of the field of view so that it intersects the Y axis orthogonally, and the measurement and fitting are executed in the same way as with the X direction, and $a_{sy}$ 862 and $LSF_{sy}$ 863 are decided.

The point spread function of scattered X-ray $PSF_s$ and the scattered X-ray intensity ratio $a_s$ are obtained from Formulas (38) and (39) (864,865).

$$PSF_s(x,y) = LSF_{sx}(x) \cdot LSF_{sy}(y) \tag{38}$$

$$a_s = (a_{sx} + a_{sy})/2 \tag{39}$$

When it can be assumed that the characteristics of the X and Y directions are approximately the same, $PSF_s(x,y)$ is decided by a single parameter.

With respect to data to be used for fitting, line data contains many statistical noises due to the X-ray quantum, so that data which is added data of a plurality of lines is used. The differentiated image has a horizontally symmetric shape. However, the noise is lower on the side shielded by the metallic plate and higher on the side not shielded by the metallic plate, so that the data on the shielded side which is turned around the peak is used.

The scattered X-ray intensity ratio and point spread function of the scattered X-ray are measured for various acrylic plates by the aforementioned method, and the relation between the acrylic plate thickness and the scattered X-ray intensity ratio is obtained. Next, a method for calculating the scattered X-ray intensity ratio used for an actual measured image from the obtained scattered X-ray intensity ratio will be explained.

The scattered X-ray intensity ratio $a_s$ depends on, as mentioned above, the tube voltage for measurement, thickness of subject, anti-scatter grid, diameter of field of view, and distance between subject and grid (called air gap) and varies with the experimental condition. Even if it is assumed that $a_s$ does not vary with the position of the field of view, it becomes a complicated function of many parameters. The reference by Honda and others (Medical Physics (1991)), discloses that the ratio $a_s$ of the scattered X-ray intensity $I_s$ of to the direct X-ray (primary X-ray) intensity $I_p$ on a measured image is expressed by Formula (40).

$$a_s = G \cdot f(A, F) \cdot (T_s/T_p) \cdot \{exp(g_1 \cdot L) - 1\} \tag{40}$$

where $T_s$ indicates a transmissivity of scattered X-ray of the anti-scatter grid, $T_p$ a transmissivity of direct X-ray of the anti-scatter grid, A an air gap, F a size of irradiation view field, f(A, F) a function of the air gap and size of irradiation view field, L a thickness of a subject, and $g_1$ a term to be obtained experimentally about the generation probability of scattered X-ray and f(1, )=1 is standardized.

In this case, G, $T_s$, $T_p$, and $g_1$ are functions of the tube voltage $V_t$. f(A, F) does not depend on the tube voltage and the thickness of subject. Therefore, parameters appearing in Formula (40) at a plurality of tube voltages $V_t$ are decided and stored in the table. For an image measured at a tube voltage not given in the table, $a_s$ is calculated by the interpolation process.

An experiment and process for obtaining $a_s$ at some tube voltages will be explained hereunder. Firstly, edge images (2 directions) are picked up at various thicknesses of acrylic plate, for example, 0, 5, 10, 15, 20, and 25 cm, under a condition of with a grid or without a grid, and at various tube voltages, for example, 60, 80, 100, and 120 kV.

Each edge image is subjected to veiling glare correction, and an LSF is obtained and fitted by two functional components, and the direct X-ray intensities $I_{po}$ and $I_p$ and the scattered X-ray intensities $I_{so}$ and $I_s$ with a grid and without a grid are obtained, and $a_s$ is obtained from these values. An actual method of this experiment and process is described already by referring to FIGS. 8 and 9. Next, the transmissivity of scattered X-ray $T_s$ and the transmissivity of direct X-ray $T_p$ of the grid are obtained from Formulas (41) and (42).

$$T_s = I_s/I_{so} \tag{41}$$

$$T_p = I_p/I_{po} \tag{42}$$

These values depend little on the thickness of acrylic plate, so that the mean value of values obtained at various thickness of acrylic plate is used. $T_s$ and $T_p$ are obtained for each different grid. Next, the thickness of acrylic plate is set on the horizontal axis, and as is set on the vertical axis, and the values are plotted. This graph is fitted by Formula (40) and the two parameters, G.f(A, F) and $g_1$ values, are decided. With respect to the air gap A and the size of irradiation view field F, the aforementioned measurement is executed for several values respectively and the data is stored in the table. The values of A and F are automatically decided or manually selected according to the measurement condition and f(A, F) is decided by the interpolation process or by others.

Furthermore, according to the method by Honda and others, L is eliminated from Formula (40) and considering that the formula is held regardless of the value of L, Formula (43) which can be applied to a subject having unknown thickness L is obtained. This formula is decided by the value of measured image and experimental condition. Hereinafter, a symbol alb indicates a power, that is, a to the b-1h power.

$$I_s = z_1(I_p^{(1-g)}) + z_2 \cdot I_p \tag{43}$$

where $z_1$, $z_2$, and g are given by Formulas (44) to (46).

$$z_1 = T_s \cdot G \cdot f(A, F) \cdot (I_o^{(g)})/(T_p^{(1-g)}) \tag{44}$$

$$z_2 = -T_s \cdot G \cdot f(A, F)/T_p \tag{45}$$

$$g = g_1/u \tag{46}$$

where u indicates an X-ray absorption coefficient. $I_o$ is obtained from Formula (47) as a digital value of the intensity of a raw beam under the standard imaging condition.

$$I_o = I_{ref} \cdot OT \cdot TC \cdot ET \cdot (100/D)^2 \qquad (47)$$

where OT indicates a transfer efficiency of the iris of the optical system, TC an X-ray tube current(A), ET a radiation duration time (ms), D a distance between X-ray tube and detectors (cm), and $I_{ref}$ a digital value of signal intensity under the standard condition (TC.ET=1 mAs, OT=1.0, D=100 cm).

To simplify calculation of the scattered X-ray correction process, the approximation of Formula (48) is used in Formula (43).

$$I_p^{(1-g)} = m \cdot I_p \qquad (48)$$

where m is expressed by Formula (49).

$$m = X_p^{(-g)} \qquad (49)$$

where $X_p$ indicates an approximate solution of $\max I_p$ (maximum value of a direct X-ray image). An approximate value of $X_p$ is obtained by a method using the maximum value of a measured image or a method using the maximum value of an image $I_q$ which is obtained by correcting a veiling glare component image from a measured image.

To obtain the approximate value of $X_p$ more accurately, the relation of Formula (50) is used.

$$I_q = I_p + I_s = z_1 \cdot (I_p^{(1-g)} + (z_2+1) \cdot I_p) \qquad (50)$$

Assuming $\max I_q$ (maximum value of a veiling glare component corrected image) as a 0-th approximate solution, the Newton method can be used $X_p$ is obtained by one of these methods and m is obtained from Formula (49). Formula (48) is substituted for Formula(43) and Formula (51) is obtained by the definition of $a_s$.

$$a_s = I_s/I_p = z_1 \cdot m + z_2 \qquad (51)$$

$a_s$ can be calculated by using a parameter measured beforehand, a condition for image measurement, and an image value.

Next, a method for calculating $a_s$, $PSF_s$, $a_v$, and $PSF_v$ to be applied to a real image by using the aforementioned parameters will be explained by referring to FIGS. 10 and 11.

Figure 10A:
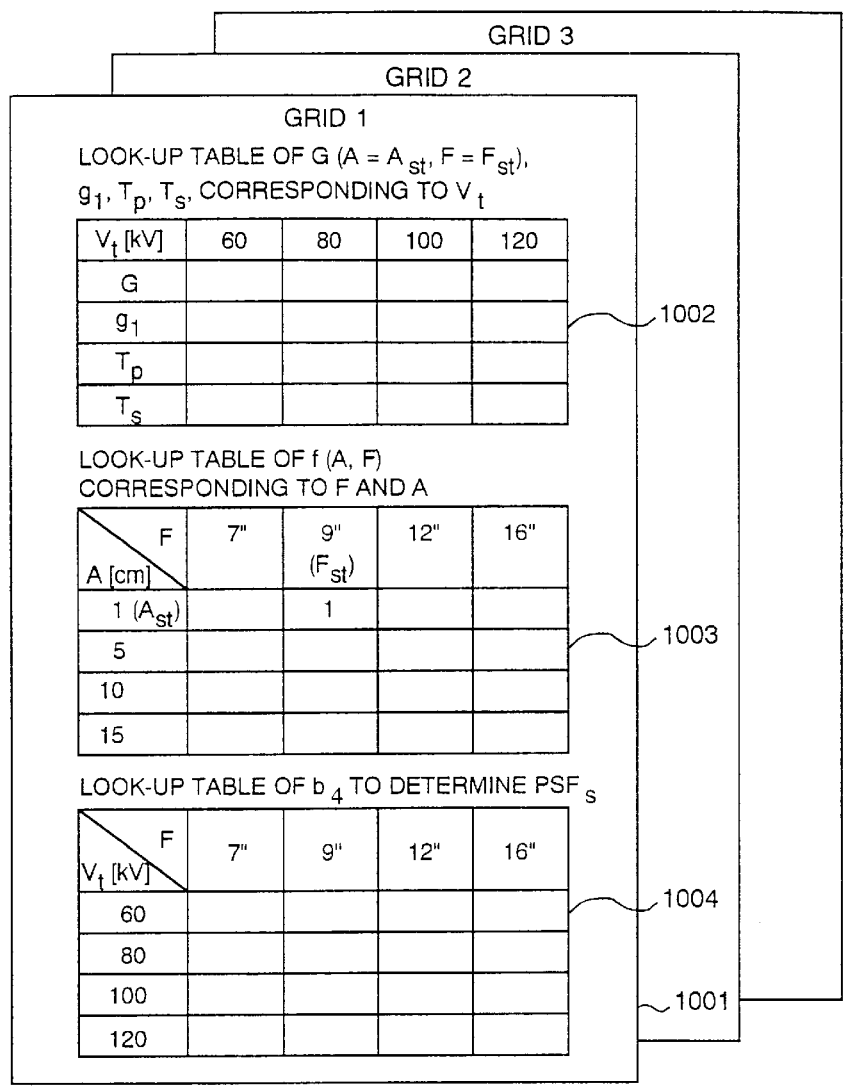
FIG. 10 is a drawing showing contents of data to be stored in a memory used by the correction process of the present invention.
Figure 10B:
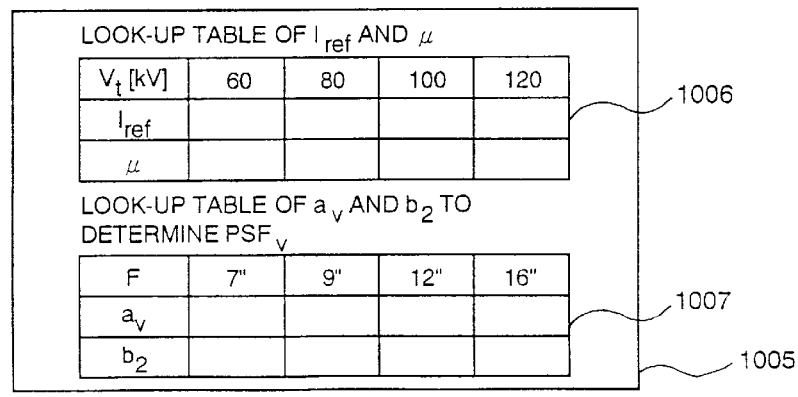

FIG. 10 shows an example of contents of data stored in a memory of a fluorographic device before actual image measurement. The memory comprises a memory unit A 1001 storing data when a specific grid is used and a memory unit B 1005 storing data which does not depend on the grid. In the memory unit A 1001, values of G, $g_1$, $T_p$, and $T_s$ obtained when the values of A and F are the standard values $A_{st}$ and $F_{st}$ respectively are stored at some X-ray tube voltages $V_t$ (1002).

The values of G and $g_1$ are decided by obtaining $a_s$ for acrylic plates with various thicknesses and executing the function fitting using Formula (40). $T_s$ and $T_p$ are calculated using Formulas (41) and (42). In the memory unit A 1001, values of f(A, F) are stored for some combinations of A and F (1003). The value of $f(A_{st}, F_{st})$ is 1.0. Values of f(A, F) expert for $f(A_{st}, F_{st})$ are expressed as a ratio of $a_s$ under each condition to $a_s$ at $A_{st}$ and $F_{st}$. In the memory unit A 1001, $b_4$ for deciding $PSF_s$ for some combinations of F and $V_t$ is stored (1004).

Next, in the memory unit B 1005, $I_{ref}$ and an X-ray absorption coefficient u at some X-ray tube voltages $V_t$ are stored (1006). Furthermore, in the memory unit B 1005, $b_2$ for deciding the veiling glare component intensity ratio $a_v$ and the point spread function of veiling glare component $PSF_v$ is stored (1007).

Figure 11:
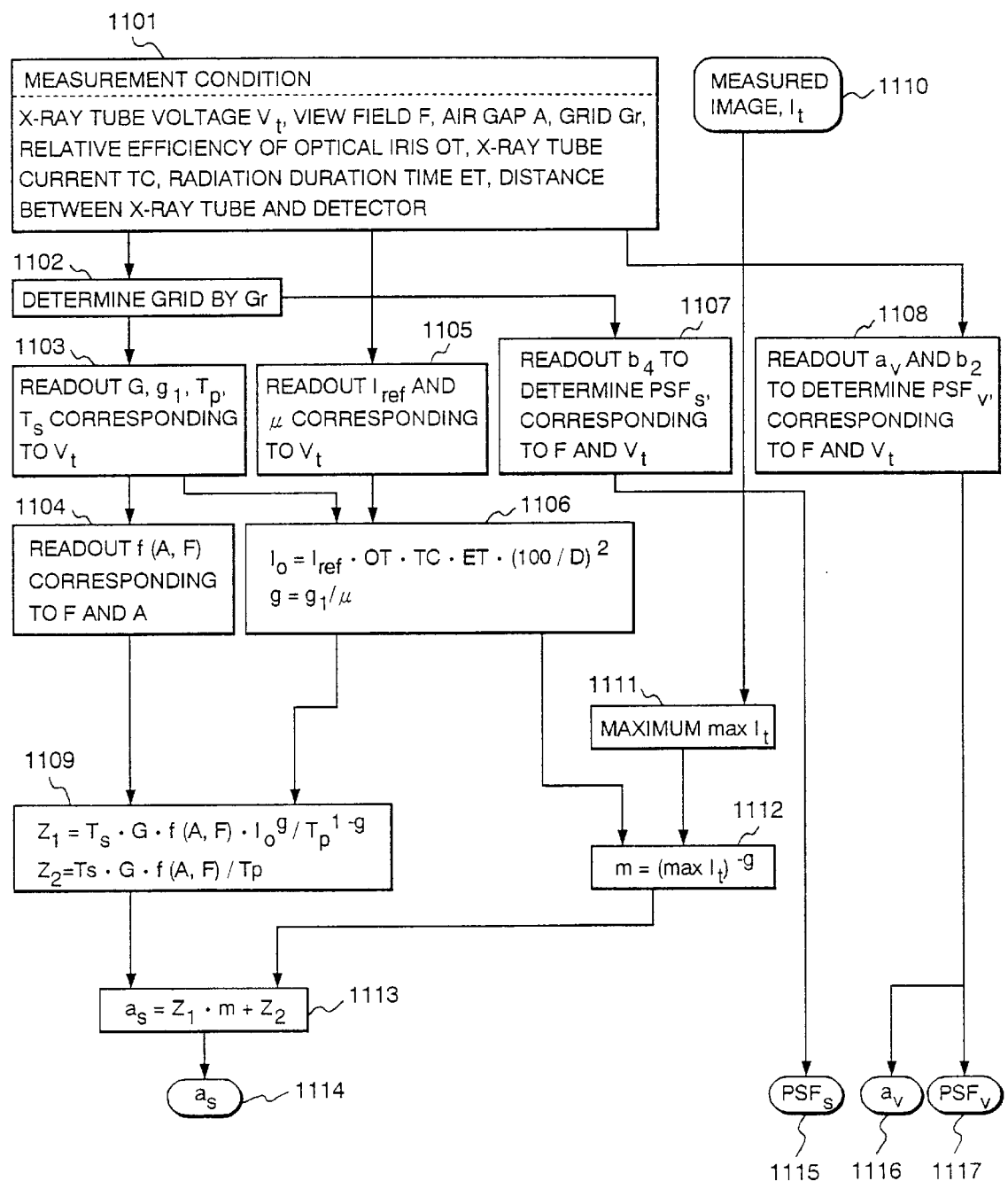
FIG. 11 is a flow chart for obtaining veiling glare and scattered X-ray intensity ratios and a point spread functions applied to a real image by the correction process of the present invention.

FIG. 11 shows an actual flow chart for deciding the values of $a_s$, $PSF_s$, $a_v$, and $PSF_v$ to be applied to a real image. As an actual image measurement condition, data of X-ray tube voltage $V_t$, size of view field F, air gap A, anti-scatter grid $G_r$, relative efficiency of the optical iris OT, X-ray tube current TC, radiation duration time ET, and distance between X-ray tube and detectors D are used (1101).

Firstly, the grid is designated by $G_r$ (1102). Next, the values of G, $g_1$, $T_p$, and $T_s$ for $V_t$ are read from the table 1002 (1103). Next the value of f(A, F) for A and F is read from the table 1003 (1104). On the other hand, the values of $I_{ref}$ and u for $V_t$ are read from the table 1006 (1105). Next Formulas (46) and (47) are processed and Ig and Io are calculated (1106). Formulas (44) and (45) are processed using these parameters and $z_1$ and $z_2$ are calculated (1109).

On the other hand, a maximum value $\max I_t$ is obtained from a measured image $I_t$ 1110 (1111) and m is obtained by replacing $X_p$ with $\max I_p$ in Formula (49) (1112). $a_s$ 1114 used for a real image is decided from Formula (51) using $z_1$, $z_2$, and m (1113).

Separately from the aforementioned process, the parameter $b_4$ is read for F and $V_t$ from the table 1004 for the designated grid (1107) and $PSF_s$ is calculated using Formulas (37) and (38) (1115). $a_v$ and the parameter $b_2$ are read for F and $V_t$ from the table 1007 (1108), and $a_v$ is used as it is (1116), and $PSF_v$ is calculated using Formulas (23) and (24) (1117).

Embodiment 4

Figure 12:
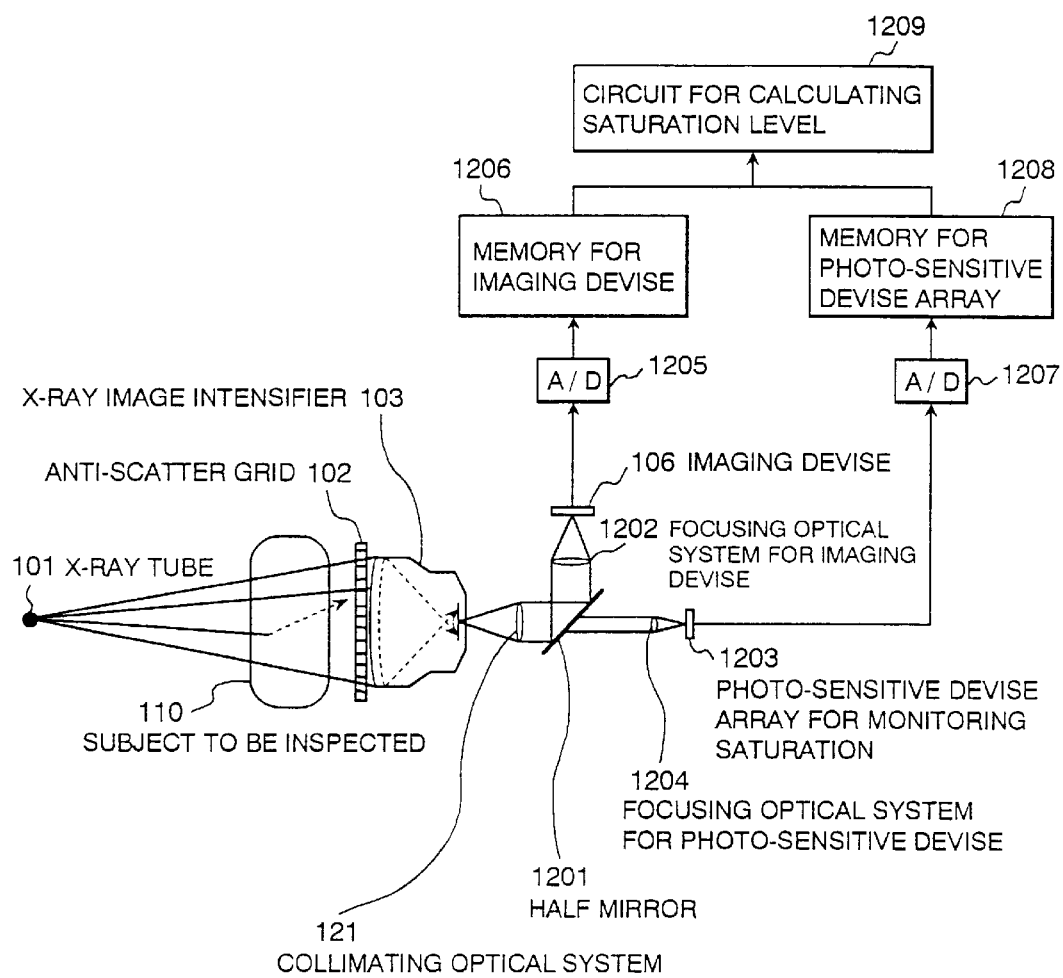
FIG. 12 is a drawing showing the constitution of a radiographic device for performing the approximate correction process when saturation occurs in the present invention.

FIG. 12 shows an embodiment of a radiographic device for performing the aforementioned correction approximately even when the output of an imaging device is saturated and halation occurs. The radiographic device comprises an X-ray tube 101, an anti-scatter grid 102, an XII 103, a collimating optical system 121, a half mirror 1201, an imaging device for performing fluorography and radiography 106, a focussing optical system for imaging device 1202, a photo-sensitive device array for monitoring saturation 1203, a focussing optical system for photo-sensitive device 1204, an A/D converter for imaging device 1205, a memory for imaging device 1206, an A/D converter for photo-sensitive device array 1207, a memory for photo-sensitive device array 1208, and a circuit for calculating saturation level 1209. In this embodiment, a CCD device of 1000×1000 pixels is used as an imaging device and a 2-dimensional photodiode array of 5×5 devices is used as a photo-sensitive device array.

The output of the photodiode is set so that it is proportional to the input even under the X-ray condition that the CCD device is saturated. In the focussing optical system for photo-sensitive device 1204, the iris is adjusted so that the output of the photo-sensitive device is not saturated. The area of 200×200 pixels of the imaging device corresponds to the area of one photo-sensitive device.

The output voltage of each photo-sensitive device is adjusted so that when the output of the imaging device reaches the saturation digital value ds, the digital converted value of output of the photo-sensitive device also reaches ds. When fluorographic images are continuously measured, the analog-digital converter for the photo-sensitive devices converts output signals of all the photo-sensitive devices to digital signals sequentially and holds newest X-ray image values of all the photo-sensitive devices on the memory.

Figure 13:
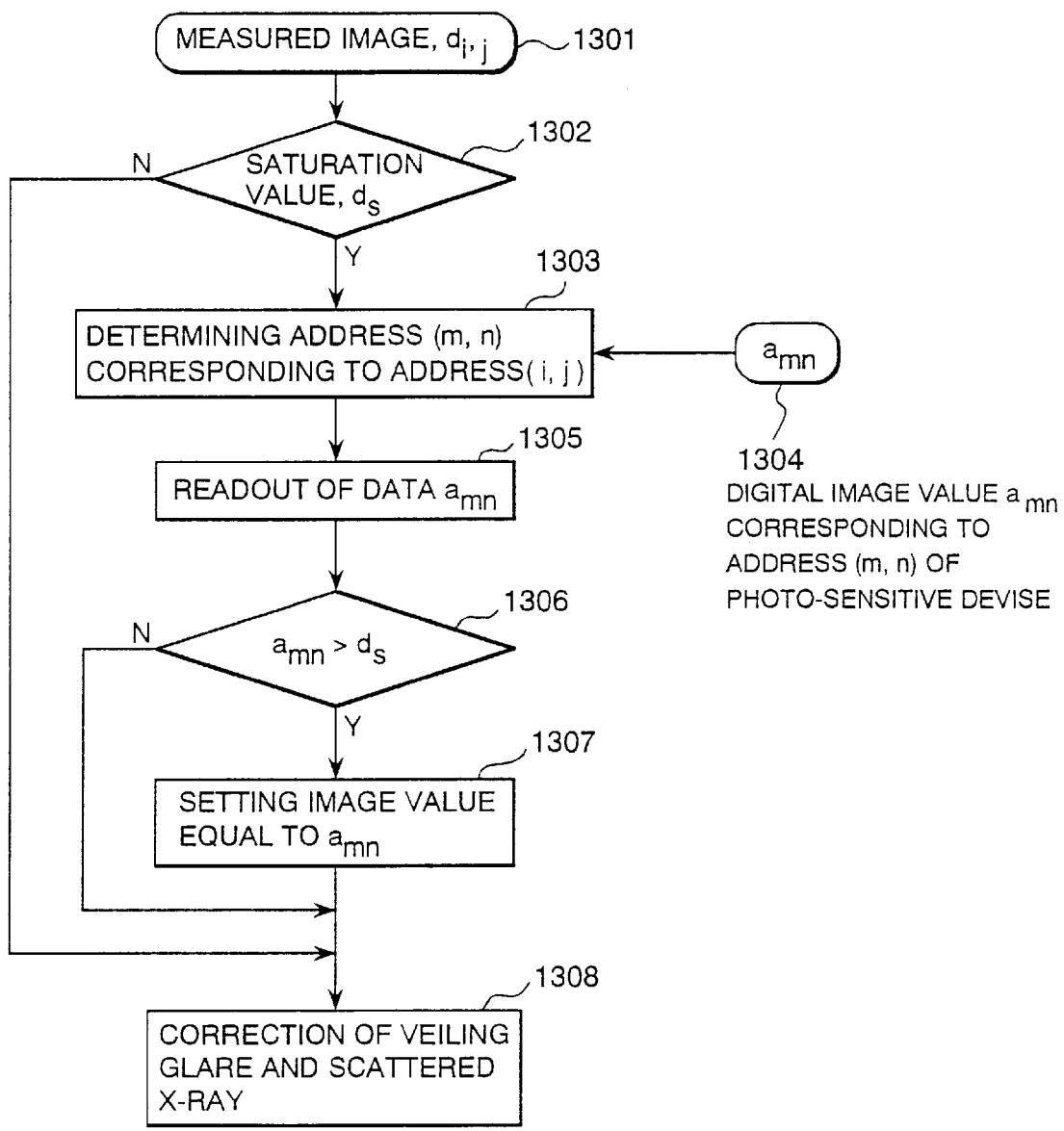
FIG. 13 is a flow chart for performing approximate correction when saturation occurs in the present invention.

The saturation correction process in the procss circuit 1209 is shown in FIG. 13. The system discriminates whether the value $d_{ij}$ 1301 at a pixel (i,j) of a measured image is equal to the saturation value ds or not (1302). When it is equal to the saturation value, the system calculates the position coordinates (m,n) of the photo-sensitive device array corresponding to the position of the pixel (i,j) of the imaging device (1303) and reads the image value ($a_{mn}$) from the memory of the photo-sensitive device (1305).

Next, the system compares $d_{ij}$ and $a_{mn}$ (1306). When $a_{mn}$ is larger than $d_{ij}$, the system changes the value of the measured image from $d_{ij}$ to ($a_{mn}$) (1307). The system performs this process for all the pixels. After this correction is executed, the system executes the correction of veiling glare and scattered X-ray which is explained before (1308). By doing this, even if the output of the imaging device is saturated and halation occurs, the system can correct both the veiling glare and scattered X-ray approximately.

Embodiment 5

Figure 14:
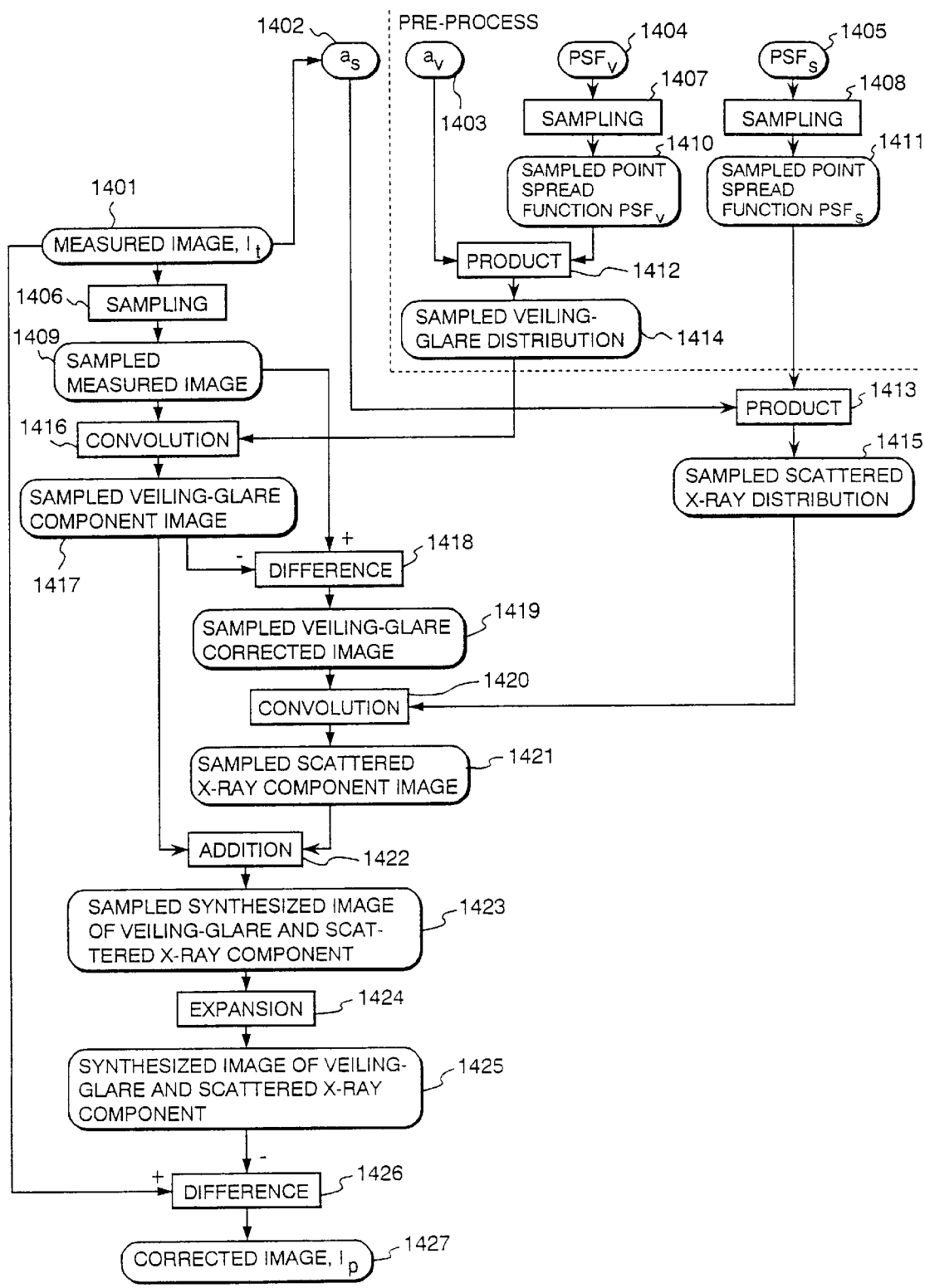
FIG. 14 is a flow chart for executing the correction process of the present invention at high speed.

FIG. 14 shows an embodiment that the correction of veiling glare and scattered X-ray can be executed at high speed even by a system having no special processor and can be applied also to a fluorographic image, an extremely fine image, and a cone beam CT which require high speed processing. In this embodiment, the same process as that of the embodiment shown in FIG. 7 is executed by performing a sampling operation, generating a reduced measured image, in which the matrix size of the measured image is reduced a reduced convolution filter in which the matrix size of the convolution filter is reduced, and performing the correction process of veiling glare and scattered X-ray using the reduced image and the reduced convolution filter in a process which amount is extremely smaller than that when the sampling operation is not performed.

In the embodiment of this sampling, a measured image comprises 1024×1024 pixels, and the sampling pitch is standardized to 16 pixels for both the measured image and convolution filter, and the size of a reduced image is 64×64.

In FIG. 14, before obtaining a measured image 1401, a point spread function of veiling glare 1404 is sampled two-dimensionally (1407) beforehand and a sampled point spread function of veiling glare 1410 is generated. A point spread function of scattered X-ray 1405 is sampled (1408) and a sampled point spread function of scattered X-ray 1411 is generated. Furthermore, as a pre-process, from a product 1412 of a veiling glare intensity ratio 1403 and the sampled point spread function of veiling glare 1410, a sampled veiling glare distribution function 1414 is obtained.

A scattered X-ray intensity ratio 1402 is obtained from a measured image 1401 and the measurement condition. This method is above-mentioned. From a product of the scattered X-ray intensity ratio 1402 and the sampled point spread function of scattered X-ray 1411, a sampled scattered X-ray distribution function 1415 is obtained. The measured image 1401 is sampled (1406) and a sampled measured image 1409 is obtained. The obtained sampled measured image 1409 and the sampled veiling glare distribution function 1414 are convoluted (1416) and a sampled veiling glare component image 1417 is obtained.

The sampled veiling glare component image 1417 is subtracted from the sampled measured image 1409 (1418), and a sampled veiling glare corrected image 1419 is obtained, and a sampled scattered X-ray component image 1421 is calculated from a convolution 1420 of this image 1419 and the sampled scattered X-ray distribution function 1415. By addition 1422 of the obtained sampled scattered X-ray component image 1421 and the sampled veiling glare component image 1417, a sampled synthesized image of veiling glare and scattered X-ray 1423 is obtained.

The image 1423 is expanded to the original matrix size by the interpolation process (1424) and a synthesized image of veiling glare and scattered X-ray component image 1425 is calculated. The synthesized image of veiling glare and scattered X-ray component 1425 is subtracted from the measured image 1401 (1426) and a corrected image 1427 is obtained. By doing this, the correction process can be executed by the convolution for a small scale image and the amount of calculation of convolution can be reduced extremely.

Figures 15A, 15B:
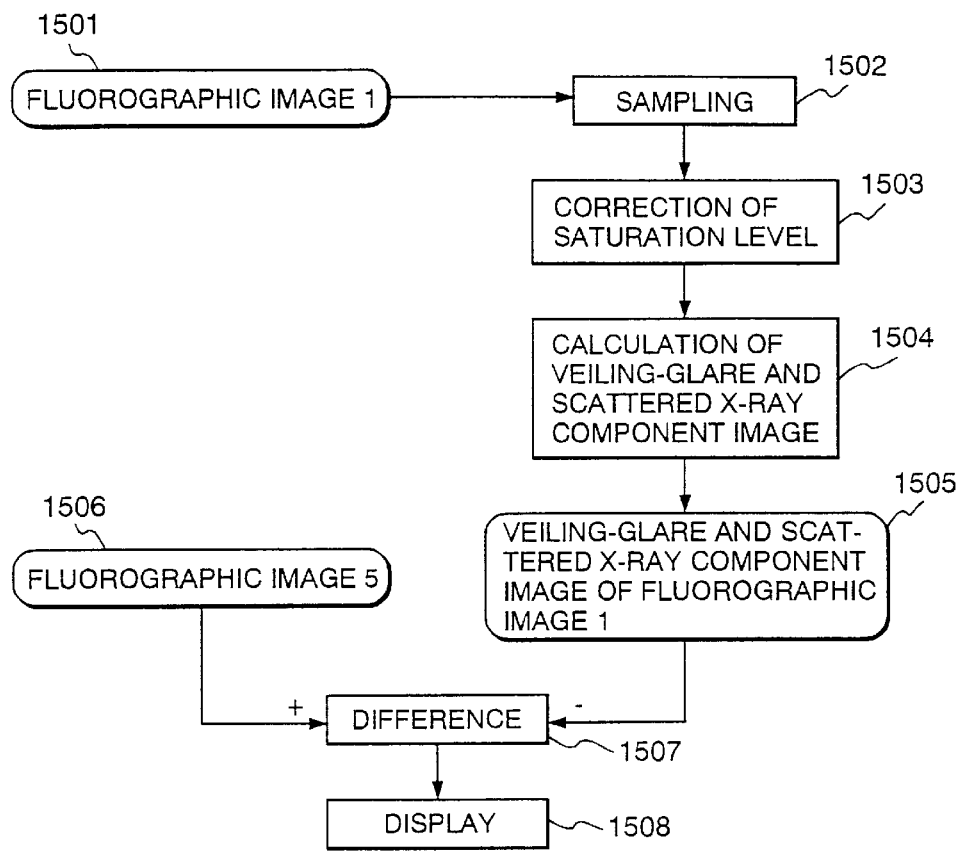
FIG. 15A is a flow chart for performing the approximate correction process for a fluorographic image in the present invention.
FIG. 15B is a drawing showing a fluorographic image, a display image, a veiling glare and scattered X-ray image used for the difference process, and a fluorographic image in the process of obtaining a correction image when the approximate correction process for a fluorographic image in the present invention is performed.

FIGS. 15A and 15B show an embodiment that a fluorographic image can be corrected approximately even if the time required for correction process is longer than the time of one frame of fluorography. In this embodiment, fluorographic images acquired continuously are sampled intermittently, and veiling glare and scattered X-ray component images are generated only for the sampled images. Hereinafter, continuous fluorographic images are referred to as a fluorographic image 1, a fluorographic image 2, a fluorographic image 3, - - - .

FIG. 15A shows an example when the calculation of a veiling glare and scattered X-ray component image requires a time between 3 and 4 frames and shows that the fluorographic image 1 (1501) is sampled 1502. The aforementioned correction of saturation level 1503 is executed for the sampled image and then the aforementioned process calculation generating veiling glare and scattered X-ray component image 1504 is executed. In this case, the process is performed by one of the method using the Fourier transformation shown in Embodiment 1, the method using the convolution shown in Embodiment 2, and the method executing spatial sampling shown in Embodiment 5. The obtained veiling glare and scattered X-ray component image 1505 is subtracted (1507) from a fluorographic image 5 (1506) to be displayed next instead of the corresponding fluorographic image 1, and the result of subtraction is displayed (1508).

FIG. 15B shows a fluorographic image to be picked up, a display image, a veiling glare and scattered X-ray component image used for the difference process, and an image in the process of obtaining a veiling glare and scattered X-ray component image. An image to be displayed is the fluorographic image itself or a difference image between the fluorographic image and the veiling glare and scattered X-ray component image. In this embodiment, the first fluorographic image (fluorographic image 1) to the fluorographic image 4 are displayed itself. During the period of time, the aforementioned sampling process to calculation process generating the veiling glare and scattered X-ray component are being executed for the fluorographic image 1. While the fluorographic image 4 is displayed, the process ends and then a difference image between the fluorographic image 5 and the veiling glare and scattered X-ray component image of fluorographic image 1 1505 is displayed (1508).

In this frame, the fluorographic image 5 is sampled at the same time and the correction process is executed sequentially. The veiling glare and scattered X-ray component image used for the fluorographic image correction process (difference process) from the fluorographic image 5 to the fluorographic image 8 still relates to the fluorographic image 1. During this period of time, the fluorographic image 5 is being sampled and the veiling glare and scattered X-ray component image is being obtained. The moment when a displayed image 9 is displayed, a process of obtaining a veiling glare and scattered X-ray image used for the difference process from the fluorographic image 5 is started. In the frames from the fluorographic image 9 to the fluorographic image 12, the the image used for generating veiling glare and scattered X-ray component image used for the difference process is kept unchanged at the fluorographic image 5.

During this period of time, the fluorographic image 9 is processed as for a next veiling glare and scattered X-ray component image. Since the component image for correction is subtracted from the newest fluorographic image to be displayed next instead of the corresponding fluorographic image, the corrected fluorographic image can be displayed in real time and can be corrected approximately.

Figure 16A:
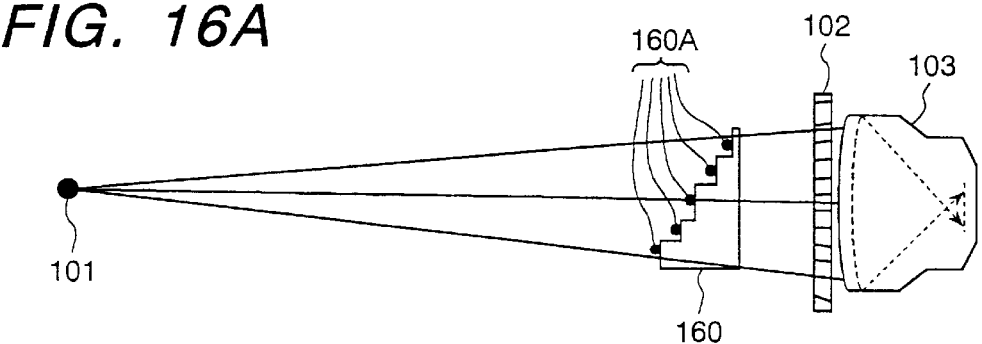
FIGS. 16A, 16B, and 16C are drawings for explaining effects of the present invention.
Figure 16B:
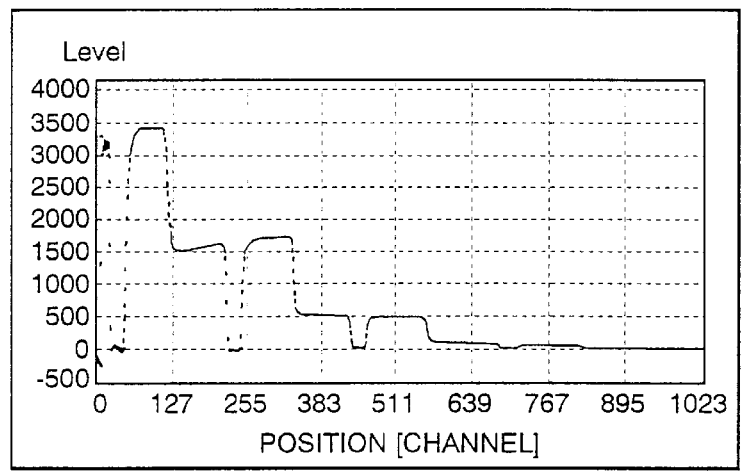

The effect of the embodiment described above will be explained hereunder. As shown in FIG. 16A, a terraced acrylic plate 160 is arranged at the location in front of an XII 103 where a subject is arranged. On each flat portion constituting the steps of the acrylic plate 160 which is different in height a metallic bar 160A (6 mm in thickness, 5 mm in width) is mounted along the longitudinal direction. This acrylic plate 160 is terraced, so that the thickness of the acrylic plate 160 through which X-rays pass from an X-ray tube 101 to the XII 103 varies with the location thereof (in this case, 1, 5, 10, 15, and 20 cm). The output changing in corresponding to the passing thickness is obtained from the XII 103 and the aforementioned correction of veiling glare and scattered X-ray component image is executed. FIG. 16B shows a profile of values of the obtained corrected image on one line in the vertical direction of the steps and FIG. 16C shows a profile of a part of the profile shown in FIG. 16B which is expanded.

Figure 16C:
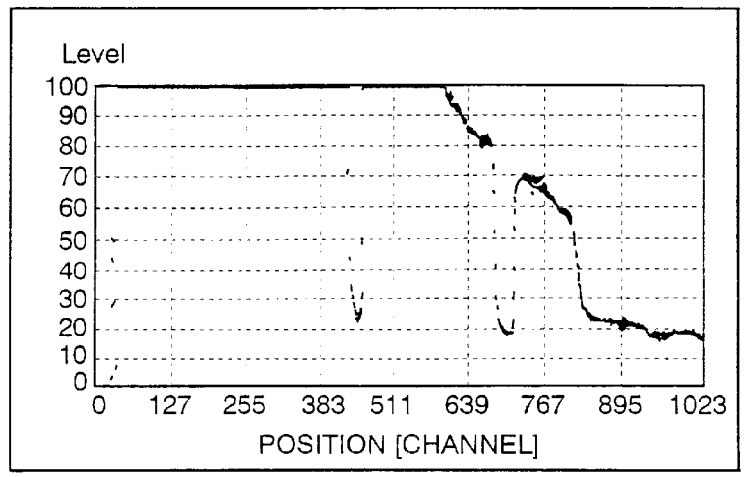
Figure 17A:
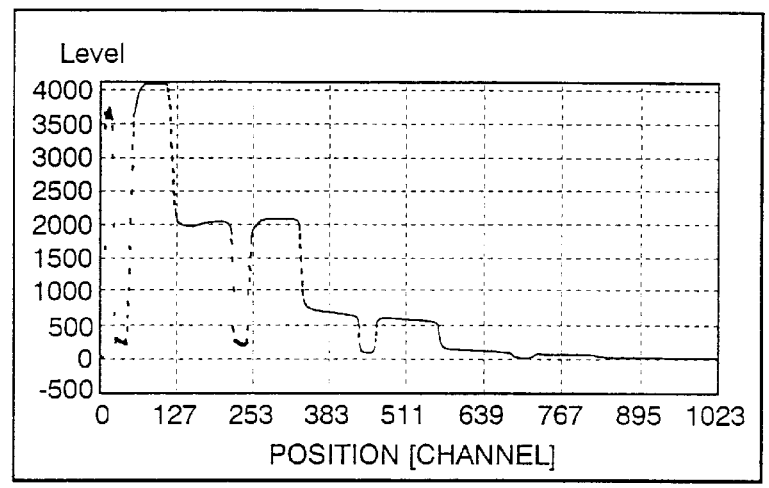
FIGS. 17a And 17b are drawings showing comparison with the effects of the present invention.
Figure 17B:
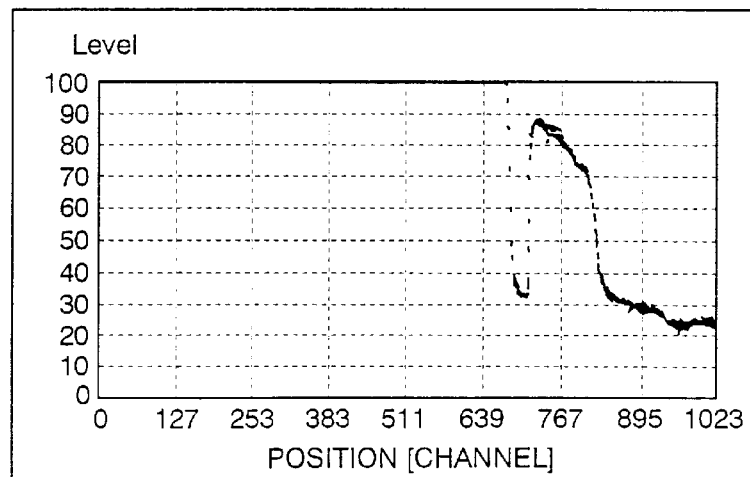

As shown in FIG. 16C, at the location where the metallic bar 160A is arranged, the level is close to 0. For reference, the drawings corresponding to FIGS. 16B and 16C when the correction of the present invention is not executed are shown in FIGS. 17A and 17B respectively. In FIGS. 17A and 17B, as compared with FIGS. 16B and 16C, at the location where the metallic bar 160A is arranged, the level is far from 0 and the difference from the aforementioned corrected image is conspicuous. Namely, in an example of an acrylic plate 10 cm in thickness, the ratio of signal (contrast) to bias component is about 5.7 in an image before correction and about 22 in an image after correction and it is improved about 3.8 times by the present invention. This indicates that the reduction of image contrast due to a scattered X-ray or veiling glare is effectively corrected by this embodiment.

In each embodiment of the present invention, with an input terminal not shown in FIG. 12, selection of the presence or absence of execution of the correction process, selection of contents of the correction process, selection of a parameter for selection of a grid, the selection of the presence or absence of correction of the parameter table, correction of contents of the parameter table, and designation of other condition parameters to be designated are inputted from the mouse or keyboard. These inputted contents are displayed on a display control screen not shown in FIG. 12. Furthermore, it is possible to execute selection of the presence or absence of execution of the correction process, designation of contents of the correction process, or designation of a parameter for selection of a grid by selecting one of the switches mounted on the control panel and display the designated contents on the display mounted on the control panel.

The present invention is explained above as an X-ray image formation method. However, the present invention includes also a fluorographic device to which this X-ray image formation method is applied. Namely, the fluorographic device comprises an X-ray tube, an anti-scatter grid, a means for converting an X-ray image to an optical image, a means for converting an optical image to an electrical signal, an analog-digital converter, a digital image acquisition device, and a digital image processor and has a first storage means for storing the relative value of intensity ratio of scattered X-ray under the fluorographic or radiographic condition, a second storage means for storing the point spread function of scattered X-ray component under the fluorographic or radiographic condition, a third storage means for storing the image value under the reference X-ray condition at the voltage of X-ray tube, a fourth storage means for storing the intensity ratio of veiling glare component and the point spread function of veiling glare component for the size of view field, and a means for correcting the veiling glare component and scattered X-ray component of a measured image using the value of the measured image and the data stored in the above storage means.

In this fluorographic device, the first storage means is a means for storing the relative value of intensity ratio of scattered X-ray for the voltage of X-ray tube and the intensity ratio (relative value) of scattered X-ray for the size of view field and air gap, and the second storage means is a means for storing the point spread function of scattered X-ray component for the size of view field and voltage of X-ray tube, and the third storage means is a means for storing the image value under the reference X-ray condition at the voltage of X-ray tube, and the fourth storage means is a means for storing the intensity ratio of veiling glare component and the point spread function of veiling glare component for the size of view field, and the first to third storage means have a means for storing an individual value for each different grid.

Furthermore, a means for converting an X-ray image to an optical image is the X II, and a means for converting an optical image to an electrical signal is a focussing optical system and an imaging device, and the focussing optical system has a means for focussing an output image of the image intensifier at two locations, a means for measuring one of the images focussed by the focussing optical system by the imaging device for measuring a fluorographic image or a radiographic image, a means for measuring the remaining one of the images focussed by the focussing optical system by the photo-sensitive device array for measuring the halation level, a means for storing the digital value of the newest image signal measured by the imaging device and the digital value of the newest output signal of each device measured by the photo-sensitive devices, a means for discriminating whether the output of the imaging device is saturated or not, a process means for correcting the output saturation level of the imaging device using the output signal of the photo-sensitive device array when the output of the imaging device is saturated, and a means for correcting both the veiling glare and the scattered X-ray after the saturation level is corrected Furthermore, the apparatus for realizing another method described in the embodiments has a means for obtaining fluorographic images continuously as digital images, a means for sampling fluorographic images intermittently, a means for generating a synthesized image of veiling glare and scattered X-ray component for sampled images, a means for subtracting the synthesized image of veiling glare and scattered X-ray component from the measured image to be displayed next and a means for displaying the result.

The present invention is not limited to the type described in the aforementioned embodiments but can be applied to a fields of radiography. As an embodiment thereof the present invention can be applied to a cone beam CT device. Namely, the cone beam CT device having a means for storing an air image in which only air is imaged, a means for correcting the veiling glare component of an air image and generating a sensitivity distribution image, a means for performing the logarithmic difference process of an image obtained by correcting the veiling glare component and the scattered X-ray component from a measured image and a sensitivity distribution image, and a means for correcting a geometrical distortion of the measurement system can reconstruct a three-dimensional image using data in which the veiling glare and scattered X-ray are corrected, so that the accuracy of CT value of an obtained CT image is improved remarkably compared with the conventional one.

As another embodiment of application of the present invention, there are a radiographic device comprising a combination of a radiographic device using an X-ray film and a film digitizer and a radiographic device using a stimulation phosphoric screen. More concretely, the present invention is applied to a radiographic device in which a means for converting an X-ray image to an optical image comprises an X-ray intensifying screen film system (first means) and a reading beam (second means) of a film digitizer for reading an optical image stored in the first means optically and a means for converting an optical image electrically is a light detection device of the film digitizer.

The present invention can be applied to another radiographic device in which a means for converting an X-ray image to an optical image is a laser beam system of a stimulation phosphoric screen reader for reading the stimulation phosphoric screen optically and a means for converting an optical image electrically is a light detection device of the stimulation phosphoric screen reader.

Embodiment 6

Figure 22:
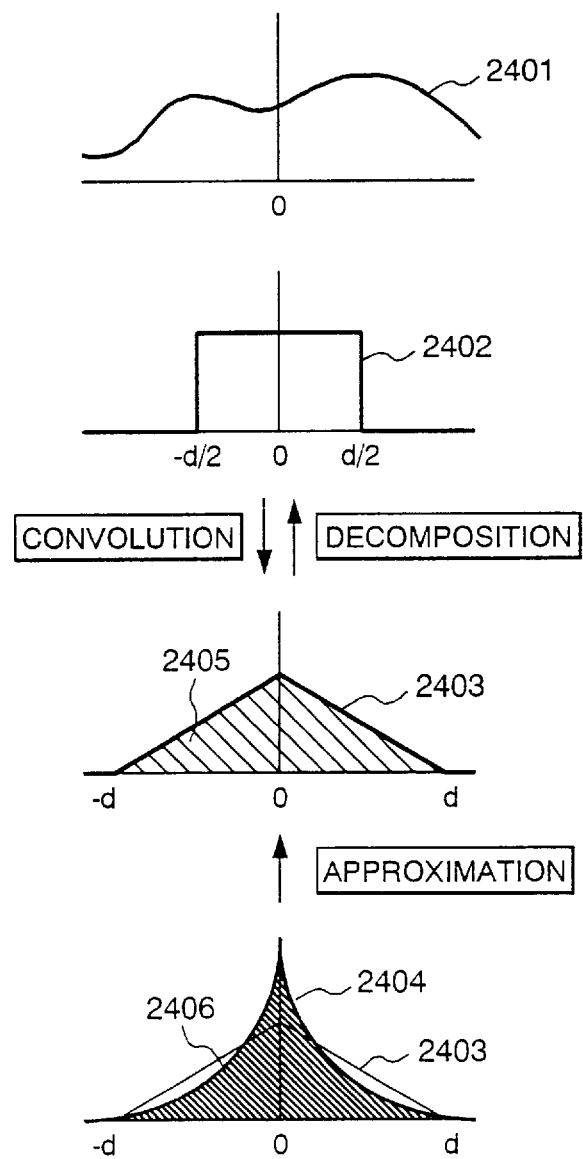
FIG. 22 is a diagram for explaining the principle of a method of approximately performing a convolution to a target filter by using a moving average calculator.
Figure 23:
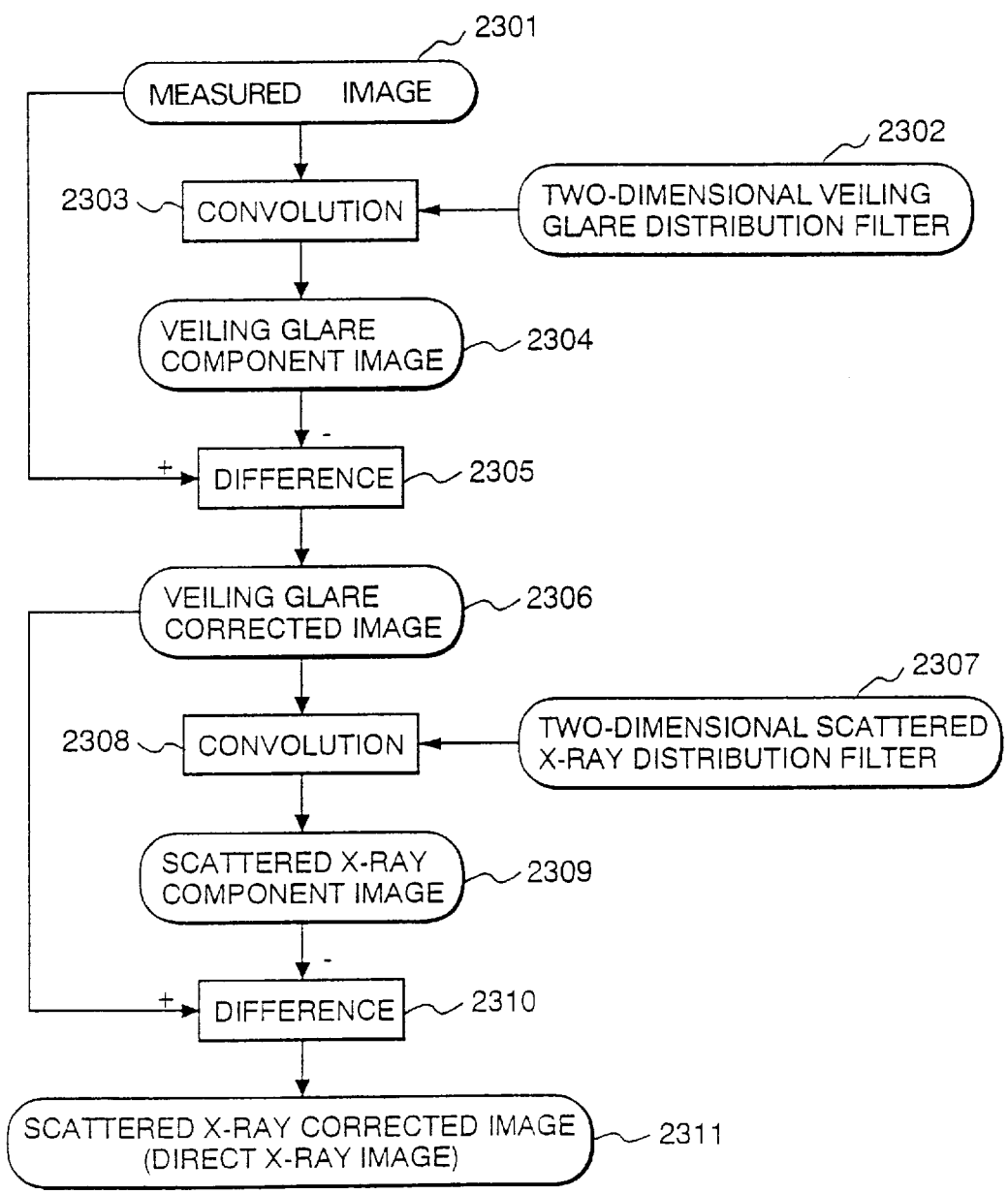
FIG. 23 is a diagram for explaining a correcting procedure of scattered X-ray and veiling glare by a conventional radiographic apparatus.

FIG. 22 is a diagram for explaining the principle of a method of approximately convoluting a filter by using a moving average calculator according to the invention. The method of approximately convoluting the filter by using the moving average calculator will be described hereinbelow with reference to FIG. 22.

In FIG. 22, reference numeral 2401 denotes measured data; 2402 a rectangular filter corresponding to moving average calculation; 2403 a triangular wave filter obtained by convoluting the same rectangular filters 2402; and 2404 a filter as a target.

It is generally known that when the rectangular filters 2402 are convoluted, the triangular wave filter 2403 is obtained. The fact that the triangular filter 2403 is obtained by convoluting the rectangular filters 2402 will be first described by using expressions. When the rectangular filter is a function p(x), the function p(x) is expressed by Formula 52.

$$p(x) = 1 \quad \left(0 < x < \left|\frac{d}{2}\right|\right) \tag{52}$$
$$= 0 \quad \left(x > \left|\frac{d}{2}\right|\right)$$

When Formula 52 is convoluted, the following Formula 53 is obtained.

$$q(x) = p(x) * p(x) \tag{53}$$

When Formula 53 is subjected to Fourier transformation, the following Formula 54 is obtained.

$$Q(f) = P(f) \cdot P(f) \tag{54}$$
$$= \left\{ 2 \cdot \int_0^{\frac{d}{2}} \cos(2\pi f x) dx \right\} \cdot$$
$$\left\{ 2 \cdot \int_0^{\frac{d}{2}} \cos(2\pi f x) dx \right\}$$
$$= \frac{\sin^2(\pi f d)}{(\pi f)^2}$$

Formula 54 is derived by Fourier transforming q(x) expressed by the following Formula 55.

$$q(x) = 1 - \frac{|x|}{d} \quad (0 < |x| < d) \tag{55}$$
$$= 0 \quad (d < |x|)$$

Consequently, when rectangular filters p(x) expressed by Formula 1 are convoluted, a triangular wave filter expressed by Formula 55 is obtained.

By convoluting the rectangular filter p(x) expressed by Formula 52 twice into the measured data by using the moving averaging calculator, the convolution of the triangular wave filter expressed by Formula 55 can be substituted.

First, the triangular wave filter 2403 is approximated to the filter 2404, the triangular wave filter 2403 is decomposed to the rectangular filter 2402, and the rectangular filter 2402 is convoluted twice for the measured data 2401, thereby enabling the convolution to the target filter to be approximately executed. As an approximating method by a triangular wave, for example, a fitting operation is executed by using the least square method so that the area 2405 of the triangular wave filter 2403 is equal to the area 2406 of the filter 2404 and the coefficient of the triangular wave is determined.

Figure 18:
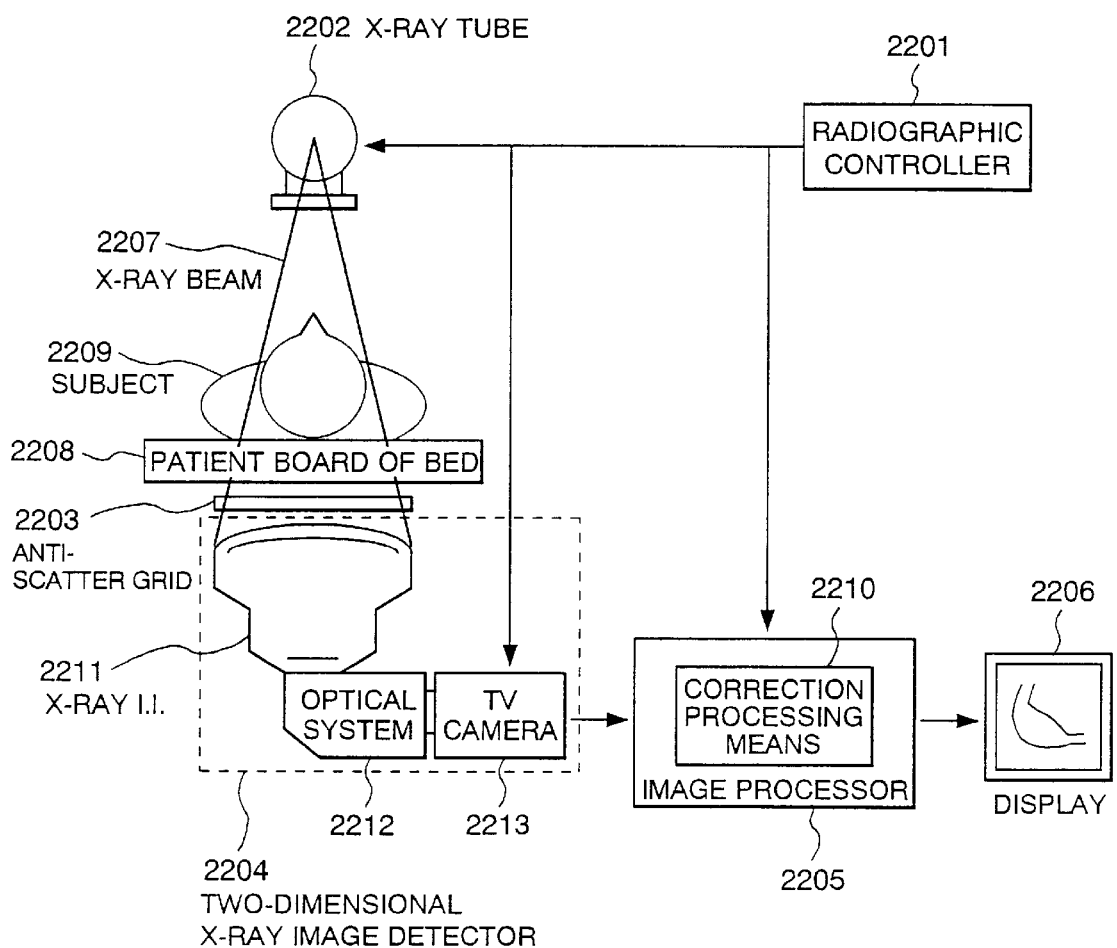
FIG. 18 is a block diagram showing a schematic construction of a fluoroscopic apparatus as a radiographic apparatus according to an embodiment of the invention.

FIG. 18 is a block diagram showing a schematic construction of a fluoroscopic apparatus as a radiographic apparatus according to an embodiment of the invention. The fluoroscopic apparatus comprises; a radiographic controller 2201, an X-ray tube 2202, an anti-scatter grid 2203, a two-dimensional X-ray image detector 2204, an image processor 2205, a display 2206, a radiation field 2207 of an X-ray, a patient board 2208 of the bed, a subject 2209, a correction processing means 2210, an X-ray I.I. 2211, an optical system 2212, and a television camera 2213.

In FIG. 18, the radiographic controller 2201 is a known radiographic controller for controlling radiation conditions such as a voltage applied to the X-ray tube 2202 and the like and imaging conditions such as an optical iris of the TV camera 2213 or the like on the basis of radiographic conditions (measurement conditions) inputted from an operation console (not shown) by an examiner. The radiographic apparatus of the embodiment outputs the radiation and imaging conditions for both of X-ray fluoroscopy and X-ray radiography to the processor 2205.

The X-ray tube 2202 is a known X-ray tube for emitting a conic X-ray beam to the subject 2209. It is obviously understood that an X-ray filter for changing an energy distribution of an X-ray beam and an X-ray collimator for regulating the radiation field 2207 of an X-ray beam can be arranged between the X-ray tube 2202 and the subject 2209.

The anti-scatter grid 2203 is a known anti-scatter grid, which is arranged in front of an input face of the X-ray I.I.2211 constructing the two-dimensional X-ray image detector 2204.

The two-dimensional image detector 2204 comprises the X-ray I.I.2211, the optical system 2212, and the TV camera 2213, transforms an intensity distribution of an X-ray transmitted the subject 2209 to an electric signal and outputs the electric signal to the processor 2205.

The image processor 2205 is a processor having a correction processing means and an image processing means for performing a known image process, and outputs and displays an image which is subjected to the image process on the display 2206. The image processor 2205 is constructed by, for example, a known A/D converter for converting an output signal of the TV camera to a digital signal and a program which operates on a known information processor for realizing the correction processing means and the image processing means. Further, the image processor 2205 stores the X-ray fluoroscopic conditions and the X-ray radiographic conditions inputted from the radiographic controller 2201 to, for instance, a storing means (not shown) connected to the image processor. It is obviously understood that when the TV camera 2213 can output a digital signal, the A/D converter is unnecessary and the signal process is performed by directly using the digital output of the TV camera 2213.

The patient board 2208 of the bed is a known board for setting an imaging position of the subject 2209. The body position of the subject 2209 to be set on the patient board 2208 is, for example, the supine position. It is obviously understood that the examiner can arbitrarily set the body position of the subject 2209 to be set on the patient board 2208 and a relative position between the patient board 2208 and the X-ray tube 2202.

The correction processing means 2210 is a correction processing means for correcting blurs caused by a veiling glare component and a scattered X-ray component included in an X-ray image of the subject 2209 acquired by the TV camera and can switch whether the correction process is executed or not on the basis of an input instruction from the operation console (not shown). The details of the correction processing means will be described hereinlater.

The X-ray I.I.2211 is a known X-ray I.I. and has, for instance, 7-, 9-, and 12-inch modes as I.I. modes. For example, the X-ray I.I.2211 of the embodiment detects X-rays in the region in a circle having the diameter of each of the inches (1 inch is 2.54 cm) on the input face.

The optical system 2212 is a known optical system for leading the optical image (X-ray image) outputted from the output face of the X-ray I.I.2211 to the TV camera 2213.

The TV camera 2213 is a known TV camera for transforming the X-ray image supplied from the optical system 2212 to electric signals. In the embodiment for example, a high resolution CCD device is used as an imaging device.

The operation of the fluoroscopic apparatus of the embodiment will be described with reference to FIG. 18.

In fluoroscopy and radiography, an X-ray beam emitted from the X-ray tube 2202 transmits the subject 2209. When the X-ray beam transmits the subject 2209, a part of the beam is scattered by the subject 2209. Although most of the scattered X-ray is shielded by the anti-scatter grid 2203, a part is not shielded and passes through the anti-scatter grid 2203. The scattered X-ray transmitted the anti-scatter grid 2203 and the direct X-ray directly transmitted the subject 2209 are simultaneously detected by the X-ray I.I.2211, transformed to an electronic image, and an image is formed on the output face and is transformed to an optical image.

In this instance, light is scattered and a veiling glare component is further added to the direct X-ray component. The light amount of the optical image is adjusted by using an optical iris (not shown) in the optical system 2212 and an image is formed on the TV camera 2213. The TV camera 2213 transforms the optical image to video signals (analog signals) and generates the video signals. The video signal outputted from the TV camera 2213 is converted to a digital signal (digital image) by an A/D converter (not shown) provided for the image processor 2205. The veiling glare component and the scattered X-ray component of the video signal converted to the digital signal that is, the digital image are removed by the correction processing means. Subsequently, the image processor 2205 performs a known image process to the digital image from which the above components have been removed and the resultant image is outputted to the display 2206 and is displayed on a display picture plane.

Especially in the radiography, the positioning is performed by using the not shown operation console so that the region of interest of the subject 2209 is positioned on a proper place of the display picture plane of the display 2206. The examiner instructs the start of radiography from the operation console at a time point when the region is positioned on the proper place, thereby storing the digital image to which the image process is performed as a radiographic image in a storing means connected to the image processor 2205.

Figure 19:
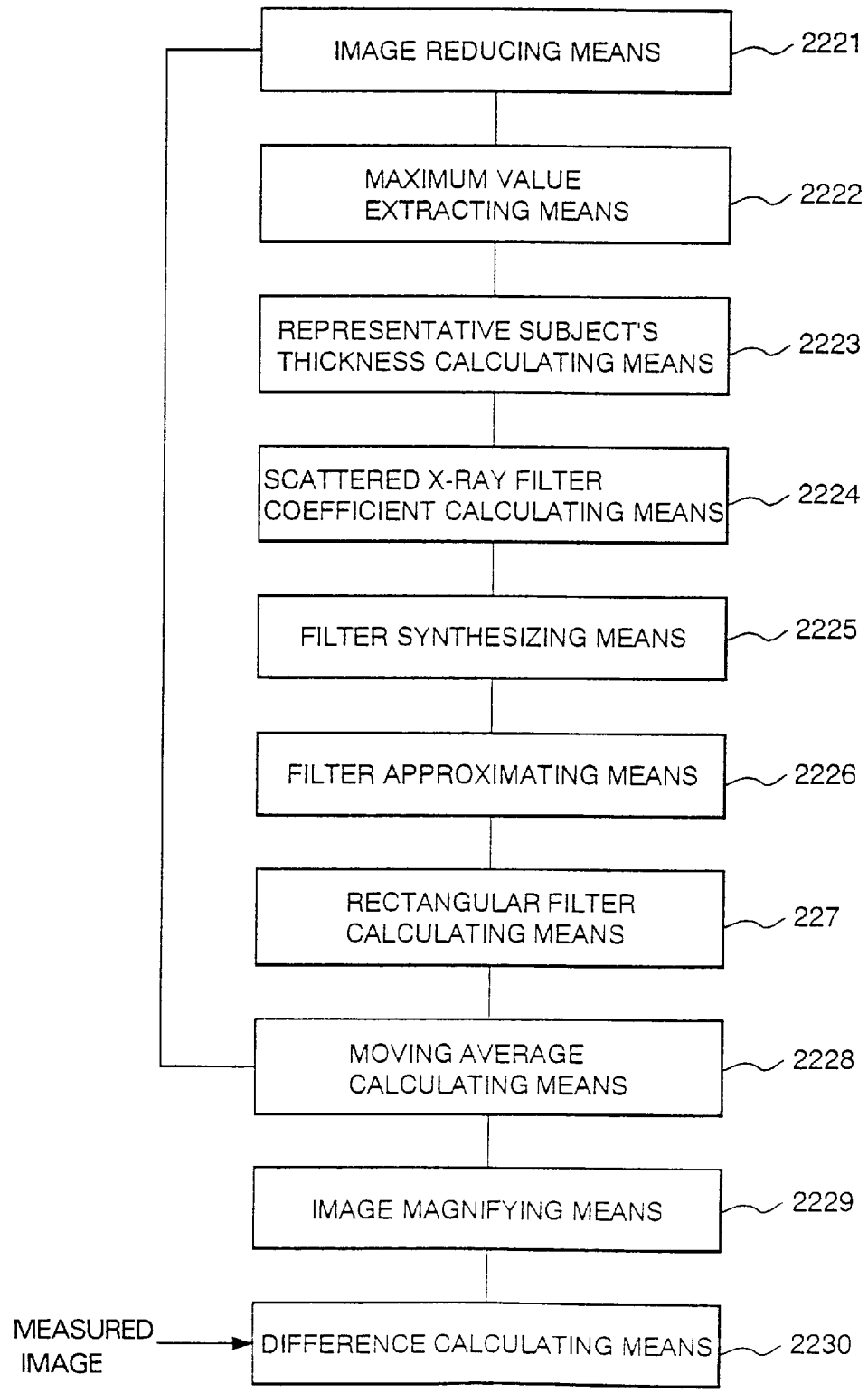
FIG. 19 is a block diagram for explaining the schematic construction of correction processing means of the embodiment.

FIG. 19 is a block diagram showing the schematic construction of the correction processing means according to the embodiment. The construction of the correction processing means will be described hereinbelow with reference to FIG. 19.

The apparatus shown in FIG. 19 comprises an image reducing means 2221, an maximum value extracting means 2222, a representative subject's thickness calculating means 2223, a scattered X-ray filter coefficient calculating means 2224 (scattered X-ray intensity distribution function forming means), a filter synthesizing means 2225, a filter approximating means 2226, a rectangular filter calculating means 2227 (window width calculating means), a moving average calculating means 2228, an image magnifying means 2229, and a difference calculating means 2230. In the embodiment, each of the means is realized by the program operating on a known information processor.

The image reducing means 2221 is a known reducing means for converting the measurement image, that is, the digital image inputted from the A/D converter (not shown) to a digital image having the number of pixels which is preset by the examiner. In the embodiment, for example, the image is reduced to a digital image of (64×64 pixels).

As mentioned above, by using not the digital image itself after the A/D conversion but the reduced digital image having the smaller number of pixels (reduced measurement image), the amount of operations which will be executed later can be reduced, so that the operation can be executed at a higher speed. The pixel size of the image to be inputted is determined by setting the camera mode. For example, in the fluoroscopy, it is assumed that the pixel size is 512 or 1024 pixels. On the other hand, it is assumed to be 1024 or 2048 pixels in the radiography. The image reducing means 2221 reduces the image by adding or thinning out (sampling) pixels to/from the image just after the A/D conversion. For example, in case of reducing the image of the size of 1024 pixels pixel addition is performed every (16×16) pixels and an average value of them is obtained or pixels are selected by thinning out every 16 pixels, the image can be reduced.

The maximum value extracting means 2222 is a known searching means for searching the maximum pixel value among pixel values of the pixels constructing the reduced measurement image, for example, by sequentially comparing the pixel values of the pixels constructing the reduced measurement image.

The representative subject's thickness calculating means 2223 is a calculating means which calculates the thickness of the subject corresponding to the inputted pixel value on the basis of a relational expression between the thickness of the subject and the pixel value. The relational expression between the thickness of the subject and the pixel value is obtained by calculating the relation between preliminarily measured acrylic plates having a plurality of thickness as a phantom and pixel values at that time by a fitting. (Refer to U.S. patent application Ser. No. 08/759,088 for the details of the calculation).

The scattered X-ray filter coefficient calculating means 2224 is a calculating means for calculating a scattered X-ray filter corresponding to an inputted thickness of the subject on the basis of the relational expression between the thickness of the phantom and the scattered X-ray filter coefficient. The relational expression between the preliminarily measured thickness of the phantom and the scattered X-ray filter coefficient is obtained by fitting the relation between the scattered X-ray filter coefficient and the thickness of the phantom. The scattered X-ray filter coefficient is obtained by calculating the product between a point spread function of a measurement value and the measurement conditions when images of the acrylic plates having a plurality of thickness as a phantom are acquired and the scattered X-ray intensity ratio as an intensity ratio of the scattered X-ray component to the direct X-ray component.(Refer to U.S. application Ser. No. 08/759,088 for the details of the calculation method).

The filter synthesizing means 2225 is a known adding means and generates a synthesized filter by adding the representative scattered X-ray filter calculated by the scattered X-ray filter coefficient calculating means 2224 and the veiling glare filter which is preliminarily calculated on the basis of the measurement conditions. The veiling glare filter 2112 is obtained by a procedure similar to the above-mentioned scattered X-ray filter, that is, by calculating the product between the point spread function of the veiling glare component and the veiling glare intensity ratio of the veiling glare component to the direct light component. The point spread function of the veiling glare component is calculated from the X-ray images, that is, the measurement conditions when the acrylic plates having a plurality of thickness as a phantom are subjected to image acquisition. (Refer to U.S. application Ser. No. 08/759,088 for the details of the calculation method).

The filter approximating means 2226 is a means for fitting the synthesized filter to the triangular wave filter by, for example, the known square least method In the embodiment, especially, the means 2226 performs the fitting so that the area of the synthesized filter and that of the triangular wave filter become equal.

The rectangular filter calculating means 2227 is a calculating means for calculating the coefficient of the rectangular filter corresponding to the inputted triangular wave filter, that is, the window width and the multiplier on the basis of the relational expression of the triangular wave filter and the rectangular filer, that is, the relational expression between the coefficient of the triangular wave filter and that of the rectangular filter. The relational expression of the triangular wave filter and the rectangular filter is preliminarily calculated by the procedure described in the article of the principle.

The moving average calculating means 2228 has a known moving average calculating means and a known multiplication means and executes a moving average calculation of the window width calculated by the rectangular filter calculating means and a multiplication of the coefficient to the result of the moving average calculation. In the embodiment, the moving average calculating means 2228 performs total four times of the moving average calculation of twice each in the lateral direction (X direction) and the vertical direction (Y direction) of the reduced measurement image.

The image magnifying means 2229 is a known interpolating means for magnifying the image obtained by the moving average calculation, that is, the reduced blur component image to form a blur component image of the original size.

The difference calculating means 2230 is a known subtracting means for subtracting the blur component image from the measured image, thereby eliminating the veiling glare and scattered X-ray components in the measured image.

Figure 20:
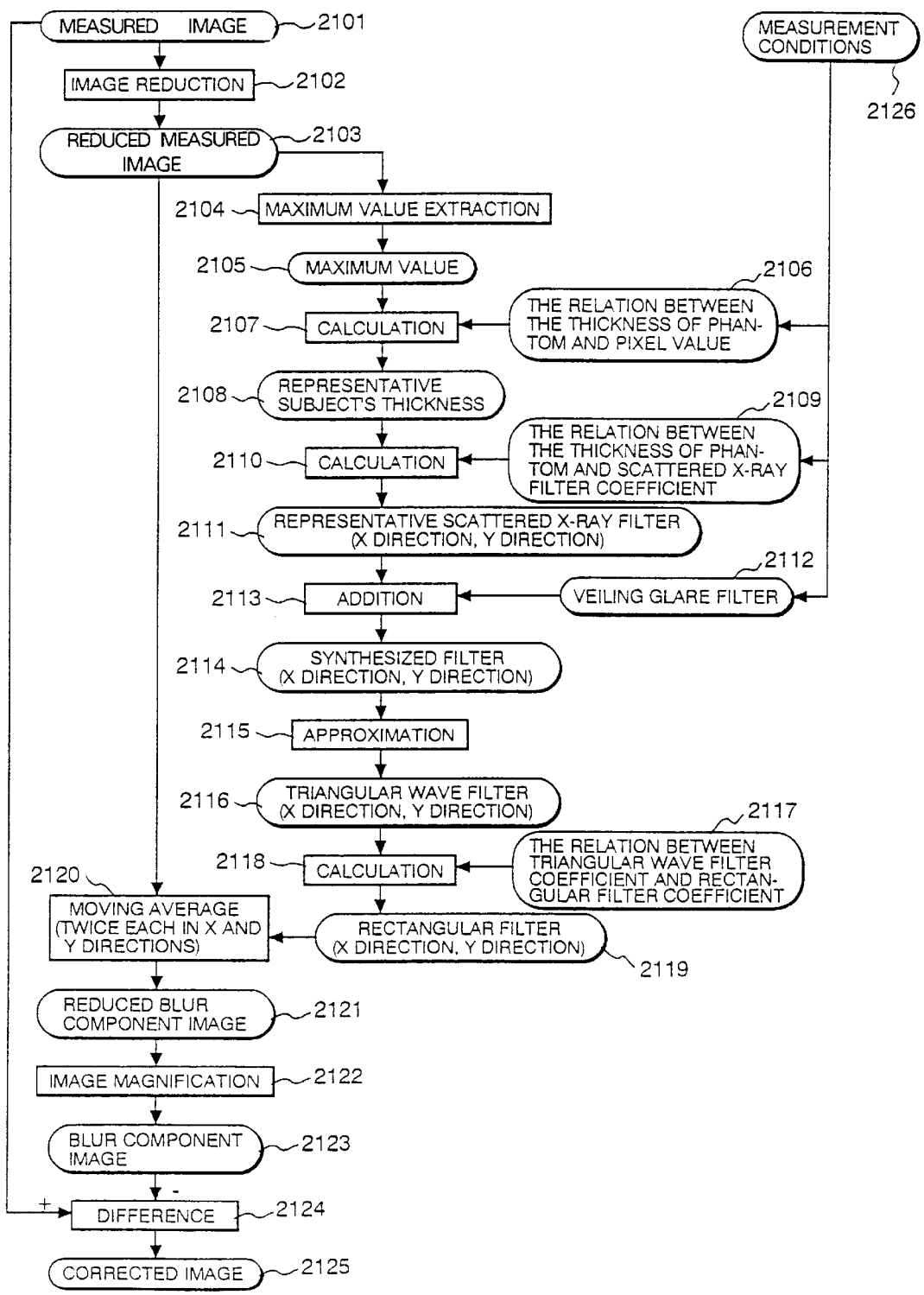
FIG. 20 is an operation flow for explaining the operation of the correction processing means of the embodiment.

FIG. 20 shows an operation flow for explaining the operation of the correction calculating means of the embodiment. The operation of the correcting means of the embodiment will be described hereinbelow with reference to FIGS. 19 and 20.

The flow starts with an input of a fluoroscopic image from the A/D converter (not shown) in the processor 2205. First, the image reducing means 2221 reduces the inputted measurement image 2101 to a reduced measurement image 2103 having pixels of the number which is preset by the examiner by sampling as a reduction calculation and the reduced measurement image 2103 is outputted to the maximum value extracting means 2222 and the moving average calculating means 2228 (step 2102).

The maximum value extracting means 2222 searches the pixels of the inputted reduced measurement image, extracts the maximum value 2105, and generates the maximum value 2105 to the representative subject's thickness calculating means 2223 (step 2104). The representative subject's thickness calculating means 2223 calculates the thickness 2108 of the subject corresponding to the maximum value 2105 (hereinbelow, written as a "representative subject thickness") on the basis of the relation between the preliminarily measured subject thickness and the pixel value (step 2107) and outputs the result of the calculation to the scattered X-ray filter coefficient calculating means 2224.

Subsequently, the scattered X-ray filter coefficient calculating means 2224 calculates a scattered X-ray filter coefficient, that is, a scattered X-ray filter 2111 corresponding to the inputted representative subject thickness on the basis of the relation between the preliminarily measured phantom thickness and the scattered X-ray filter coefficient (step 2110) and outputs the result of the calculation to the filter synthesizing means 2225. The filter synthesizing means 2225 generates a synthesized filter 2114 (2404) shown in FIG. 22 by synthesizing, that is, adding the representative scattered X-ray filter 2111 and the veiling glare filter 2112 which is preliminarily calculated on the basis of the measurement conditions and outputs it to the filter approximating means 2226. Since the point spread function of the veiling glare component and the veiling glare intensity ratio are determined by the measurement conditions, the veiling glare filter 2112 is predetermined in the embodiment.

Subsequently, the filter approximating means 2226 approximates the synthesized filter to a triangular wave filter 2116 on the basis of the filter coefficient of the synthesis filter 2114 (step 2115) and outputs the filter 2116 to the rectangular filter calculating means 2227. The rectangular filter calculating means 2227 calculates a rectangular filter (coefficient of the rectangular filter) 2119, that is, the window width and the coefficient from the inputted triangular wave filter (coefficient of the triangular wave filter) 2116 on the basis of the relation between the triangular wave filter and the rectangular filter (step 2118) and outputs the result of the calculation to the moving average calculating means 2228. The moving average calculating means 2228 reads out the reduced measurement image 2103, executes the moving average calculation of the inputted window width in the lateral direction (X direction) and the vertical direction (Y direction) to the reduced measurement image 2103, and multiplies a coefficient to the calculated image (step 2120), thereby enabling a blur component image of the reduced measurement image 2103, that is, a reduced blur component image 2121 to be obtained The image magnifying means 229 interpolates between the pixels of the reduced blur component image 2121 (step 2122), thereby forming a blur component image 2123 having the same pixel number, that is, the same size as that of the measurement image 2101. The difference calculating means 2230 calculates the difference between the read measurement image 2101 and the blur component image 2123 (step 2124), thereby enabling a corrected image 2125, that is, an X-ray image obtained by correcting the blur in the measurement image 2101 caused by the scattered X-ray components and the veiling glare components to be obtained at a high speed.

Figure 21:
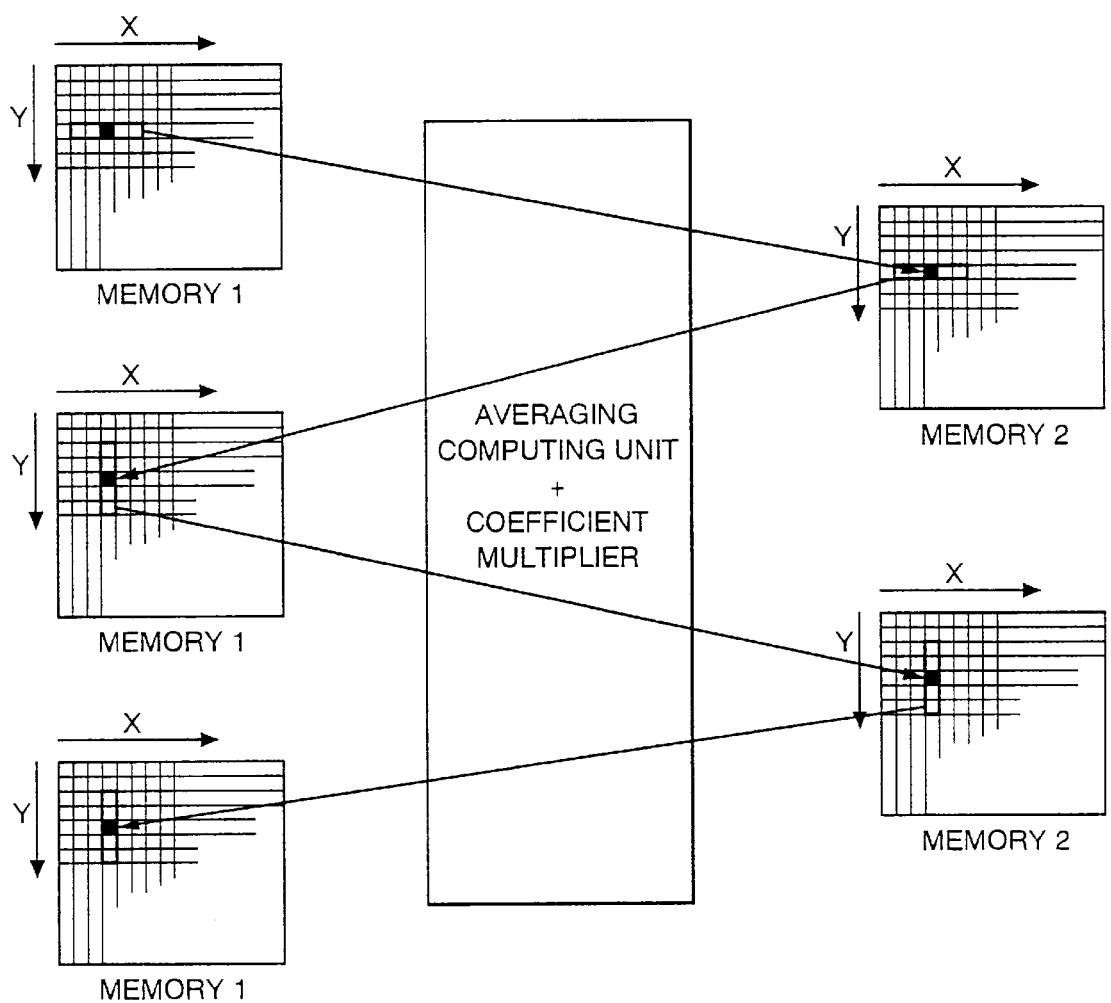
FIG. 21 is a diagram for explaining the concept of moving average calculation.

FIG. 21 is a diagram for explaining the concept of the above-mentioned moving average calculation. As shown in FIG. 21, the reduced blur component image 2121 can be formed only by executing the moving average calculation twice each in the lateral direction (X direction) and the vertical direction (Y direction) of the reduced measurement image 2103 stored in a memory by the moving average calculating means 2228.

A case of correcting, for example, an X-ray image of (500×500 pixels) by using the convolution shown in Literature 4 and a case of correcting the image by using the radiographic apparatus of the invention will be examined. In the radiographic apparatus of the invention, a case in which a triangular wave 2116 having 200 pixels of the width of the bottom (d=100 in FIG. 21) is obtained from the X-ray image will be examined. In its case, as will be obviously understood from FIG. 21, the width of the rectangular filter, that is, the window width has 100 pixels (since the width becomes ½ when the rectangular filter is decomposed in FIG. 21).

When time required for image correction under the above-mentioned conditions was simulated, time required for image correction can be reduced to almost 1/90 in the case where the invention is applied as compared with the case using the convolution. That is, by applying the invention, it was found that an image can be corrected 90 times higher.

The invention can be also applied to real-time image correction such as X-ray fluoroscopic exposure requiring an image reading rate of 30 frames per second, to which the conventional technique cannot be applied since a few second order of correction time is conventionally necessary. Even in a case such that a real-time process such as X-ray fluoroscopic exposure which cannot be accurately corrected conventionally is required, by using the radiographic apparatus of the invention, the X-ray fluoroscopic and radiographic exposures in which a blur caused by the scattered X-ray component and/or the veiling glare component is corrected can be performed.

As mentioned above, according to the radiographic apparatus of the embodiment, in the process for forming the blur component image 2123 from the measured image 2101, the filter approximating means 2226 approximates the synthesis filter 2114 obtained by synthesizing the scattered X-ray filter and the veiling glare filter to the triangular wave filter 2116 and the rectangular filter calculating means 2227 converts the triangular wave filter 2116 to the rectangular filter 2119, thereby enabling the convolution necessary to execute when the blur component image 2123 is calculated from the measured image 2101 to be replaced by the moving average calculation which can be executed at high speed.

Consequently, the blur component image 2123 can be formed at high speed. Since the correction image 2125 can be formed by obtaining the difference between the measurement image 2101 and the blur component image 2125, the correction image 2125 can be formed at high speed. In the radiographic apparatus of the embodiment, since the measured image 2101 is corrected by using the point spread function, multiplication using a high-pass filter or the like which is employed by the conventional radiographic apparatus is unnecessary, so that increase in high-frequency noises can be prevented.

Consequently, the corrected image 2125 obtained by correcting the blur component of the measured image 2101 can be formed at high speed.

Although the operation and effects when the invention is applied to the X-ray fluoroscopic apparatus have been described in the embodiment the invention is not limited to the above. For example, in a cone-beam CT apparatus for displaying a slice image, a three-dimensional image, and the like of the subject by reconstructing X-ray images acquired around the subject when the invention is applied, each of the X-ray images acquired around the subject is corrected by the above-mentioned procedure and reconstruction calculation is executed by using the corrected images, the correction time of the scattered X-ray component and the veiling glare component can be shortened and an occurrence of a deviation in the CT number in a reconstructed image caused by the scattered X-ray component and the veiling glare component included in each X-ray image can be prevented, so that diagnosis accuracy of a doctor or the like can be improved.

In the embodiment, each of the relation between the thickness of the phantom and the pixel value when the representative subject's thickness 2108 is calculated, the relation between the phantom thickness and the scattered X-ray filter when the representative scattered X-ray filter 2111 is formed, and the relation between the triangular wave filter 2116 and the rectangular filter 2119 is calculated on the basis of the relational expression calculated by fitting.

However, the invention is not limited to the above. For example, it will be obviously understood that it is also possible that relations before fitting (the thickness of the phantom and the pixel value, the thickness of the phantom and the coefficient of the scattered X-ray filter, and the coefficient of the triangular wave filter 2116 and the coefficient of the rectangular filter 2119) are stored as table data and a necessary value is generated by, for example, a known interpolation or the like from the closest value in the event of reference.

Although the window width is obtained by the movement average calculation on the basis of the synthesized filter obtained by synthesizing the scattered X-ray filter and the veiling glare filter in the embodiment, obviously, it is also possible that the window width is calculated on the basis of each of the scattered X-ray filter and the veiling glare filter and the moving average calculation is executed on the basis of each of the window widths.

Although the triangular wave filter is formed by convoluting the rectangular filters once in the embodiment, a more complicated filter shape such as a curve of the second order can be also formed by repeatingly convoluting the rectangular filter. That is, by repeatingly convoluting the rectangular filter, a complicated filter convolution can be replaced Further, although the embodiment has the construction in which the representative scattered X-ray filter is calculated on the basis of the maximum pixel value in order to eliminate the blur components most, the invention is not limited to the construction. For example, by providing the maximum value extracting means 2104 with a known range designating means for reading only pixel values within a range designated by the examiner from the operation console (not shown) or by providing a known input means for inputting the maximum pixel value by the examiner (not shown) directly from the operation console, the correction amount of the blur components can be changed according to the preference of the examiner. Since the blur component and the pixel value has a proportional relation, except for the pixel value as a reference, a pixel in which the blur component is over-corrected and a pixel in which the blur component is insufficiently corrected exist. Consequently, the examiner has the preference regarding the picture quality such as adjustment of the contrast.

Although the invention realized by the inventors has been specifically described on the basis of the embodiment, the invention is not limited by the foregoing embodiment of the invention. It will be obviously understood that the invention can be variously changed within the scope without departing from the gist.

The effects obtained by representative inventions among the inventions disclosed in the specification will be briefly described as follows.

(1) The picture quality of the X-ray fluoroscopic image or the X-ray radiographic image can be improved at high speed.

(2) A blur caused by the scattered X-ray in the X-ray fluoroscopic image or the X-ray radiographic image can be corrected at high speed.

(3) A blur caused by the veiling glare in the X-ray fluoroscopic image or the X-ray radiographic image can be corrected at high speed.

(4) The picture quality of the three-dimensional reconstructed image obtained by the three-dimensional reconstruction can be improved.

(5) The uniformity of the CT number of the three-dimensional reconstructed image obtained by the three-dimensional reconstruction can be improved.

What is claimed is:

1. A radiographic apparatus acquiring an X-ray fluoroscopic image or an X-ray radiographic image and having scattered X-ray correcting means for eliminating a scattered X-ray component from the acquired X-ray fluoroscopic image or X-ray radiographic image, the scattered X-ray correcting means comprising:

scattered X-ray intensity distribution function generating means for generating a scattered X-ray intensity distribution function on the basis of said acquired X-ray fluoroscopic image or X-ray radiographic image;

moving average calculating means for executing moving average calculation a plurality of times in each of the vertical and lateral directions of the acquired X-ray fluoroscopic image or X-ray radiographic image;

window width calculating means for calculating a window width of the moving average calculation on the basis of the scattered X-ray intensity distribution function; and difference calculating means for calculating the difference between said acquired X-ray fluoroscopic image or X-ray radiographic image and an image to which the moving average calculation is executed.

2. The radiographic apparatus according to claim 1, wherein said moving average calculating means is means for executing moving average calculation twice each in the vertical direction and in the lateral direction by the same window width.

3. The radiographic apparatus according to claim 1, further comprising image reducing means for reducing the acquired X-ray fluoroscopic image or X-ray radiographic image to an image size which is preset by the examiner, wherein each of said correcting means generates each intensity distribution function and calculates the moving average window width on the basis of the reduced image.

4. A radiographic apparatus acquiring an X-ray fluoroscopic image or an X-ray radiographic image and having veiling glare correcting means for eliminating a veiling glare component from the acquired X-ray fluoroscopic image or X-ray radiographic image, the veiling glare correcting means comprising:

veiling glare intensity distribution function generating means for generating a veiling glare intensity distribution function;

moving average calculating means for executing moving average calculation a plurality of times in each of the vertical and lateral directions of the acquired X-ray fluoroscopic image or X-ray radiographic image;

window width calculating means for calculating a window width of the moving average calculation on the basis of the veiling glare intensity distribution function; and difference calculating means for calculating the difference between the acquired X-ray fluoroscopic image or X-ray radiographic image and an image to which the moving average calculation is executed.

5. The radiographic apparatus according to claim 1, wherein said moving average calculating means is means for executing moving average calculation twice each in the vertical direction and in the lateral direction the same window width.

6. The radiographic apparatus according to claim 4, further comprising image reducing means for reducing the acquired X-ray fluoroscopic image or X-ray radiographic image to an image size which is preset by the examiner, wherein each of said correcting means generates each intensity distribution function and calculates the moving average window width on the basis of said reduced image.

7. A radiographic apparatus acquiring an X-ray fluoroscopic image or an X-ray radiographic image and having a blur component correcting means for eliminating a scattered X-ray component and a veiling glare component from the acquired X-ray fluoroscopic image or X-ray radiographic image, the blur component correcting means comprising:

scattered X-ray intensity distribution function generating means for generating a scattered X-ray intensity distribution function on the basis of the acquired X-ray fluoroscopic image or X-ray radiographic image;

veiling glare intensity distribution function generating means for generating a veiling glare intensity distribution function;

moving average calculating means for executing moving average calculation a plurality of times in each of the vertical and lateral directions of the acquired X-ray fluoroscopic image or X-ray radiographic image;

window width calculating means for calculating a window width of the moving average calculation on the basis of the scattered X-ray intensity distribution function and the veiling glare intensity distribution function; and difference calculating means for calculating the difference between the acquired X-ray fluoroscopic image or X-ray radiographic image and an image to which the moving average calculation is executed.

8. The radiographic apparatus according to claim 7, wherein said moving average calculating means is means for executing moving average calculation twice each in the vertical direction and in the lateral direction by the same window width.

9. The radiographic apparatus according to claim 7, further comprising image reducing means for reducing the acquired X-ray fluoroscopic image or X-ray radiographic image to an image of a value which is preset by the examiner, wherein each of said correcting means generates each intensity distribution function and calculates the moving average window width on the basis of said reduced image.

10. The radiographic apparatus according to claim 9, further comprising image magnifying means for magnifying the reduced image to an image of the size of the acquired X-ray fluoroscopic image or X-ray radiographic image, wherein said difference calculating means calculates the difference between an image obtained by magnifying an image derived in such a manner that said moving average calculating means executes moving average calculation a plurality of times each in the vertical direction and the lateral direction of said reduced image and the acquired X-ray fluoroscopic image or X-ray radiographic image.

11. A radiographic apparatus and an X-ray CT apparatus for reconstructing a slice image or a three-dimensional image of a subject on the basis of an X-ray radiographic image acquired around said subject, comprising.

scattered X-ray intensity distribution function generating means for generating a scattered X-ray intensity distribution function on the basis of the acquired X-ray radiographic image;

veiling glare intensity distribution function generating means for generating a veiling glare intensity distribution function;

moving average calculating mean for performing moving average calculation a plurality of times each in the vertical direction and the lateral direction of the acquired X-ray radiographic image;

window width calculating means for calculating the window width of the moving average calculation on the basis of the scattered X-ray intensity distribution function and the veiling glare intensity distribution function; and difference calculating means for calculating the difference between the acquired X-ray fluoroscopic image or X-ray radiographic image and an image to which the moving average calculation is performed.

* * * * *